United States Patent
Katz et al.

(10) Patent No.: US 10,471,098 B2
(45) Date of Patent: Nov. 12, 2019

(54) HEPATIC ARTERIAL INFUSION OF CAR-T CELLS

(71) Applicant: Prospect CharterCare RWMC, LLC, Providence, RI (US)

(72) Inventors: Steven C. Katz, Providence, RI (US); Richard Junghans, Boston, MA (US)

(73) Assignee: PROSPECT CHARTERCARE RWMC, LLC, Providence, RI (US)

( * ) Notice: Subject to any disclaimer, the term of this patent is extended or adjusted under 35 U.S.C. 154(b) by 39 days.

(21) Appl. No.: 15/099,370

(22) Filed: Apr. 14, 2016

(65) Prior Publication Data

US 2016/0303166 A1  Oct. 20, 2016

Related U.S. Application Data

(60) Provisional application No. 62/147,793, filed on Apr. 15, 2015.

(51) Int. Cl.

| | |
|---|---|
| *A61K 39/395* | (2006.01) |
| *A61K 35/17* | (2015.01) |
| *A61K 9/00* | (2006.01) |
| *A61K 38/20* | (2006.01) |
| *A61K 45/06* | (2006.01) |
| *C07K 14/00* | (2006.01) |
| *C12N 5/0783* | (2010.01) |

(52) U.S. Cl.
CPC ............ *A61K 35/17* (2013.01); *A61K 9/0019* (2013.01); *A61K 38/2013* (2013.01); *A61K 45/06* (2013.01); *C07K 14/00* (2013.01); *C12N 5/0636* (2013.01); *C12N 2510/00* (2013.01)

(58) Field of Classification Search
None
See application file for complete search history.

(56) References Cited

U.S. PATENT DOCUMENTS

| | | |
|---|---|---|
| 2002/0165360 A1 | 11/2002 | Junghans |
| 2012/0134970 A1 | 5/2012 | Yang et al. |

FOREIGN PATENT DOCUMENTS

| | | |
|---|---|---|
| WO | WO 2014/055668 A1 | 4/2014 |
| WO | WO 2014/134165 A1 | 9/2014 |

OTHER PUBLICATIONS

Kemeny et al, J Clin Oncol, 24:1395-1403, 2006.*
Kemeny et al, J Clin Oncol, 2:595-600, 1984.*
Parkhurst et al, Mol Ther, 19:620-626, 2011.*
Burga et al., "Liver myeloid-derived suppressor cells expand in response to liver metastases in mice and inhibit the anti-tumor efficacy of anti-CEA CAR-T", Cancer Immunol. Immunther., vol. 64, No. 7, pp. 817-829 (2015).
Clark and Smith, "Liver-directed therapies in metastatic colorectal cancer", J. Gastrointest. Oncol., vol. 5, No. 5, pp. 374-387 (2014).
Emtage et al., "Second-generation anti-carcinoembryonic antigen designer T cells resist activation-induced cell death, proliferate on tumor contact, secrete cytokines, and exhibit superior antitumor activity in vivo: a preclinical evaluation", Clin. Cancer Res., Vil. 14, No. 24; pp. 8112-8122 (2008).
Grover et al., "The past decade of experience with isolated hepatic perfusion", The Oncologist, vol. 9, No. 6, pp. 653-664 (2004).
International Search Report from International Patent Application No. PCT/US2016/027582 dated Jul. 27, 2016.
Katz et al., "Regulatory T Cell Infiltration Predicts Outcome Following Resection of Colorectal Cancer Liver Metastases", Ann. Surg. Oncol., vol. 20, No. 3, pp. 946-955 (2013).
Katz et al., "Phase I Hepatic Immunotherapy for Metastases Study of Intra-Arterial Chimeric Antigen Receptor-Modified T-cell Therapy for CEA+ Liver Metastases", Clin. Cancer Res., vol. 21, No. 14. pp. 3149-3159 (2015).
Khan et al., "The Prognostic Value of Liver Tumor T Cell Infiltrates", J. Surg. Res., vol. 191. No. 1, pp. 189-195 (2014).
Parkhurst et al., "T Cells Targeting Carcinoembryonic Antigen Can Mediate Regression of Metastatic Colorectal Cancer but Induce Severe Transient Colitis", Molecular Therapy, vol. 19, No. 3, pp. 620-626 (2011).
Sadelain et al., "The basic principles of chimeric antigen receptor (CAR) design", Cancer Discov. vol. 3, No. 4 pp. 388-398 (2013).
Saied et al., "Regional hepatic therapies: an important component in the management of colorectal cancer liver metastases", Hepatobility Surg. Nutr., vol. 2, No. 2, pp. 97-107 (2013).
Saied et al., "Neutrophil:lymphocyte ratios and serum cytokine changes after hepatic artery chimeric antigen receptor modified T cell infusions for liver metastases", Cancer Gene Ther., vol. 21, No. 11, pp. 457-462 (2014).
Weiss et al., "Regulatory T Cells and Myeloid-Derived Suppressor Cells in the Tumor Microenvironment Undergo Fas-Dependent Cell Death during IL-2/aCD40 Therapy", J. Immunol., vol. 192, pp. 5821-5829 (2014).
Katz et al., Abstract CT109 with accompanying poster: HITM-SIR: Phase 1b trial of CAR-T hepatic artery infusions and selective internal radiation therapy for liver metastases. Proceedings: AACR Annual Meeting 2017; Apr. 1-5, 2017; Washington, DC.
Daly, John M., et al. "Long-term Hepatic Arterial Infusion Chemotherapy" pp. 936-941. Arch Surg—vol. 119, Aug. 1984.

* cited by examiner

*Primary Examiner* — Mark Halvorson
(74) *Attorney, Agent, or Firm* — McDermott Will & Emery LLP

(57) ABSTRACT

Disclosed herein are compositions and methods for the treatment of liver metastases in a subject. The methods include hepatic arterial infusion (HAI) of chimeric antigen receptor modified T cells (CAR-T) which are highly specific for tumor antigens such as carcinoembryonic antigen (CEA). The HAI method is optimized to maximize exposure of the modified cells to the metastatic cells while minimizing exposure to healthy cells. The methods include co-administration of a second therapeutic agent, such as IL-2.

15 Claims, 6 Drawing Sheets
Specification includes a Sequence Listing.

SEQUENCE LISTING

```
<160> NUMBER OF SEQ ID NOS: 6

<210> SEQ ID NO 1
<211> LENGTH: 213
<212> TYPE: PRT
<213> ORGANISM: artificial
<220> FEATURE:
<223> OTHER INFORMATION: Synthetic

<400> SEQUENCE: 1
```

```
Asp Ile Gln Leu Thr Gln Ser Pro Ser Ser Leu Ser Ala Ser Val Gly
1               5                   10                  15

Asp Arg Val Thr Ile Thr Cys Lys Ala Ser Gln Asp Val Gly Thr Ser
            20                  25                  30

Val Ala Trp Tyr Gln Gln Lys Pro Gly Lys Ala Pro Lys Leu Leu Ile
        35                  40                  45

Tyr Trp Thr Ser Thr Arg His Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Ser Leu Tyr Arg Ser
                85                  90                  95

Phe Gly Gln Gly Thr Lys Val Glu Ile Lys Arg Thr Val Ala Ala Pro
                100                 105                 110

Ser Val Phe Ile Phe Pro Pro Ser Asp Glu Gln Leu Lys Ser Gly Thr
            115                 120                 125

Ala Ser Val Val Cys Leu Leu Asn Asn Phe Tyr Pro Arg Glu Ala Lys
        130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
                180                 185                 190

Cys Glu Val Thr His Gln Gly Leu Ser Ser Pro Val Thr Lys Ser Phe
            195                 200                 205

Asn Arg Gly Glu Cys
    210

<210> SEQ ID NO 2
<211> LENGTH: 235
<212> TYPE: PRT
<213> ORGANISM: Homo sapiens

<400> SEQUENCE: 2

Met Ala Leu Pro Val Thr Ala Leu Leu Leu Pro Leu Ala Leu Leu Leu
1               5                   10                  15

His Ala Ala Arg Pro Ser Gln Phe Arg Val Ser Pro Leu Asp Arg Thr
            20                  25                  30

Trp Asn Leu Gly Glu Thr Val Glu Leu Lys Cys Gln Val Leu Leu Ser
        35                  40                  45

Asn Pro Thr Ser Gly Cys Ser Trp Leu Phe Gln Pro Arg Gly Ala Ala
    50                  55                  60

Ala Ser Pro Thr Phe Leu Leu Tyr Leu Ser Gln Asn Lys Pro Lys Ala
65                  70                  75                  80

Ala Glu Gly Leu Asp Thr Gln Arg Phe Ser Gly Lys Arg Leu Gly Asp
                85                  90                  95

Thr Phe Val Leu Thr Leu Ser Asp Phe Arg Arg Glu Asn Glu Gly Tyr
                100                 105                 110

Tyr Phe Cys Ser Ala Leu Ser Asn Ser Ile Met Tyr Phe Ser His Phe
            115                 120                 125

Val Pro Val Phe Leu Pro Ala Lys Pro Thr Thr Thr Pro Ala Pro Arg
        130                 135                 140

Pro Pro Thr Pro Ala Pro Thr Ile Ala Ser Gln Pro Leu Ser Leu Arg
```

```
                145                 150                 155                 160
Pro Glu Ala Cys Arg Pro Ala Ala Gly Gly Ala Val His Thr Arg Gly
                165                 170                 175
Leu Asp Phe Ala Cys Asp Ile Tyr Ile Trp Ala Pro Leu Ala Gly Thr
                180                 185                 190
Cys Gly Val Leu Leu Ser Leu Val Ile Thr Leu Tyr Cys Asn His
            195                 200                 205
Arg Asn Arg Arg Val Cys Lys Cys Pro Arg Pro Val Val Lys Ser
            210                 215                 220
Gly Asp Lys Pro Ser Leu Ser Ala Arg Tyr Val
225                 230                 235

<210> SEQ ID NO 3
<211> LENGTH: 384
<212> TYPE: PRT
<213> ORGANISM: Homo sapiens

<400> SEQUENCE: 3

Met Lys Trp Lys Ala Leu Phe Thr Ala Ala Ile Leu Gln Ala Gln Leu
1               5                   10                  15
Pro Ile Thr Glu Ala Gln Ser Phe Gly Leu Leu Asp Pro Lys Leu Cys
                20                  25                  30
Tyr Leu Leu Asp Gly Ile Leu Phe Ile Tyr Gly Val Ile Leu Thr Ala
            35                  40                  45
Leu Phe Leu Arg Val Lys Phe Ser Arg Ser Ala Asp Ala Pro Ala Tyr
        50                  55                  60
Gln Gln Gly Gln Asn Gln Leu Tyr Asn Glu Leu Asn Leu Gly Arg Arg
65                  70                  75                  80
Glu Glu Tyr Asp Val Leu Asp Lys Arg Arg Gly Arg Asp Pro Glu Met
                85                  90                  95
Gly Gly Lys Pro Gln Arg Arg Lys Asn Pro Gln Glu Gly Leu Tyr Asn
            100                 105                 110
Glu Leu Gln Lys Asp Lys Met Ala Glu Ala Tyr Ser Glu Ile Gly Met
        115                 120                 125
Lys Gly Glu Arg Arg Arg Gly Lys Gly His Asp Gly Leu Tyr Gln Gly
        130                 135                 140
Leu Ser Thr Ala Thr Lys Asp Thr Tyr Asp Ala Leu His Met Gln Ala
145                 150                 155                 160
Leu Pro Pro Arg Met Leu Arg Leu Leu Leu Ala Leu Asn Leu Phe Pro
                165                 170                 175
Ser Ile Gln Val Thr Gly Asn Lys Ile Leu Val Lys Gln Ser Pro Met
            180                 185                 190
Leu Val Ala Tyr Asp Asn Ala Val Asn Leu Ser Cys Lys Tyr Ser Tyr
        195                 200                 205
Asn Leu Phe Ser Arg Glu Phe Arg Ala Ser Leu His Lys Gly Leu Asp
        210                 215                 220
Ser Ala Val Glu Val Cys Val Val Tyr Gly Asn Tyr Ser Gln Gln Leu
225                 230                 235                 240
Gln Val Tyr Ser Lys Thr Gly Phe Asn Cys Asp Gly Lys Leu Gly Asn
                245                 250                 255
Glu Ser Val Thr Phe Tyr Leu Gln Asn Leu Tyr Val Asn Gln Thr Asp
            260                 265                 270
Ile Tyr Phe Cys Lys Ile Glu Val Met Tyr Pro Pro Pro Tyr Leu Asp
        275                 280                 285
```

```
Asn Glu Lys Ser Asn Gly Thr Ile Ile His Val Lys Gly Lys His Leu
    290                 295                 300
Cys Pro Ser Pro Leu Phe Pro Gly Pro Ser Lys Pro Phe Trp Val Leu
305                 310                 315                 320
Val Val Val Gly Gly Val Leu Ala Cys Tyr Ser Leu Leu Val Thr Val
                325                 330                 335
Ala Phe Ile Ile Phe Trp Val Arg Ser Lys Arg Ser Arg Leu Leu His
            340                 345                 350
Ser Asp Tyr Met Asn Met Thr Pro Arg Arg Pro Gly Pro Thr Arg Lys
        355                 360                 365
His Tyr Gln Pro Tyr Ala Pro Pro Arg Asp Phe Ala Ala Tyr Arg Ser
    370                 375                 380
```

<210> SEQ ID NO 4
<211> LENGTH: 220
<212> TYPE: PRT
<213> ORGANISM: Homo sapiens

<400> SEQUENCE: 4

```
Met Leu Arg Leu Leu Leu Ala Leu Asn Leu Phe Pro Ser Ile Gln Val
1               5                   10                  15
Thr Gly Asn Lys Ile Leu Val Lys Gln Ser Pro Met Leu Val Ala Tyr
                20                  25                  30
Asp Asn Ala Val Asn Leu Ser Cys Lys Tyr Ser Tyr Asn Leu Phe Ser
            35                  40                  45
Arg Glu Phe Arg Ala Ser Leu His Lys Gly Leu Asp Ser Ala Val Glu
        50                  55                  60
Val Cys Val Val Tyr Gly Asn Tyr Ser Gln Gln Leu Gln Val Tyr Ser
65                  70                  75                  80
Lys Thr Gly Phe Asn Cys Asp Gly Lys Leu Gly Asn Glu Ser Val Thr
                85                  90                  95
Phe Tyr Leu Gln Asn Leu Tyr Val Asn Gln Thr Asp Ile Tyr Phe Cys
            100                 105                 110
Lys Ile Glu Val Met Tyr Pro Pro Tyr Leu Asp Asn Glu Lys Ser
        115                 120                 125
Asn Gly Thr Ile Ile His Val Lys Gly Lys His Leu Cys Pro Ser Pro
130                 135                 140
Leu Phe Pro Gly Pro Ser Lys Pro Phe Trp Val Leu Val Val Val Gly
145                 150                 155                 160
Gly Val Leu Ala Cys Tyr Ser Leu Leu Val Thr Val Ala Phe Ile Ile
                165                 170                 175
Phe Trp Val Arg Ser Lys Arg Ser Arg Leu Leu His Ser Asp Tyr Met
            180                 185                 190
Asn Met Thr Pro Arg Arg Pro Gly Pro Thr Arg Lys His Tyr Gln Pro
        195                 200                 205
Tyr Ala Pro Pro Arg Asp Phe Ala Ala Tyr Arg Ser
    210                 215                 220
```

<210> SEQ ID NO 5
<211> LENGTH: 526
<212> TYPE: PRT
<213> ORGANISM: Homo sapiens

<400> SEQUENCE: 5

```
Met Gly His Leu Ser Ala Pro Leu His Arg Val Arg Val Pro Trp Gln
1               5                   10                  15
```

```
Gly Leu Leu Leu Thr Ala Ser Leu Leu Thr Phe Trp Asn Pro Pro Thr
             20                  25                  30

Thr Ala Gln Leu Thr Thr Glu Ser Met Pro Phe Asn Val Ala Glu Gly
         35                  40                  45

Lys Glu Val Leu Leu Leu Val His Asn Leu Pro Gln Gln Leu Phe Gly
     50                  55                  60

Tyr Ser Trp Tyr Lys Gly Glu Arg Val Asp Gly Asn Arg Gln Ile Val
 65                  70                  75                  80

Gly Tyr Ala Ile Gly Thr Gln Gln Ala Thr Pro Gly Pro Ala Asn Ser
                 85                  90                  95

Gly Arg Glu Thr Ile Tyr Pro Asn Ala Ser Leu Leu Ile Gln Asn Val
            100                 105                 110

Thr Gln Asn Asp Thr Gly Phe Tyr Thr Leu Gln Val Ile Lys Ser Asp
        115                 120                 125

Leu Val Asn Glu Glu Ala Thr Gly Gln Phe His Val Tyr Pro Glu Leu
    130                 135                 140

Pro Lys Pro Ser Ile Ser Ser Asn Asn Ser Asn Pro Val Glu Asp Lys
145                 150                 155                 160

Asp Ala Val Ala Phe Thr Cys Glu Pro Glu Thr Gln Asp Thr Thr Tyr
                165                 170                 175

Leu Trp Trp Ile Asn Asn Gln Ser Leu Pro Val Ser Pro Arg Leu Gln
            180                 185                 190

Leu Ser Asn Gly Asn Arg Thr Leu Thr Leu Ser Val Thr Arg Asn
        195                 200                 205

Asp Thr Gly Pro Tyr Glu Cys Glu Ile Gln Asn Pro Val Ser Ala Asn
    210                 215                 220

Arg Ser Asp Pro Val Thr Leu Asn Val Thr Tyr Gly Pro Asp Thr Pro
225                 230                 235                 240

Thr Ile Ser Pro Ser Asp Thr Tyr Tyr Arg Pro Gly Ala Asn Leu Ser
                245                 250                 255

Leu Ser Cys Tyr Ala Ala Ser Asn Pro Pro Ala Gln Tyr Ser Trp Leu
            260                 265                 270

Ile Asn Gly Thr Phe Gln Gln Ser Thr Gln Glu Leu Phe Ile Pro Asn
        275                 280                 285

Ile Thr Val Asn Asn Ser Gly Ser Tyr Thr Cys His Ala Asn Asn Ser
    290                 295                 300

Val Thr Gly Cys Asn Arg Thr Thr Val Lys Thr Ile Ile Val Thr Glu
305                 310                 315                 320

Leu Ser Pro Val Val Ala Lys Pro Gln Ile Lys Ala Ser Lys Thr Thr
                325                 330                 335

Val Thr Gly Asp Lys Asp Ser Val Asn Leu Thr Cys Ser Thr Asn Asp
            340                 345                 350

Thr Gly Ile Ser Ile Arg Trp Phe Phe Lys Asn Gln Ser Leu Pro Ser
        355                 360                 365

Ser Glu Arg Met Lys Leu Ser Gln Gly Asn Thr Thr Leu Ser Ile Asn
    370                 375                 380

Pro Val Lys Arg Glu Asp Ala Gly Thr Tyr Trp Cys Glu Val Phe Asn
385                 390                 395                 400

Pro Ile Ser Lys Asn Gln Ser Asp Pro Ile Met Leu Asn Val Asn Tyr
                405                 410                 415

Asn Ala Leu Pro Gln Glu Asn Gly Leu Ser Pro Gly Ala Ile Ala Gly
            420                 425                 430

Ile Val Ile Gly Val Val Ala Leu Val Ala Leu Ile Ala Val Ala Leu
```

```
                        435                 440                 445
Ala Cys Phe Leu His Phe Gly Lys Thr Gly Arg Ala Ser Asp Gln Arg
    450                 455                 460

Asp Leu Thr Glu His Lys Pro Ser Val Ser Asn His Thr Gln Asp His
465                 470                 475                 480

Ser Asn Asp Pro Pro Asn Lys Met Asn Glu Val Thr Tyr Ser Thr Leu
                485                 490                 495

Asn Phe Glu Ala Gln Gln Pro Thr Gln Pro Thr Ser Ala Ser Pro Ser
                500                 505                 510

Leu Thr Ala Thr Glu Ile Ile Tyr Ser Glu Val Lys Lys Gln
            515                 520                 525

<210> SEQ ID NO 6
<211> LENGTH: 19
<212> TYPE: PRT
<213> ORGANISM: Homo sapiens

<400> SEQUENCE: 6

Met Gly Trp Ser Cys Ile Ile Leu Phe Leu Val Ala Thr Ala Thr Gly
1               5                   10                  15

Val His Ser
```

HEPATIC ARTERIAL INFUSION OF CAR-T CELLS

CROSS-REFERENCE TO RELATED APPLICATIONS

This application claims the benefit of U.S. Provisional Application No. 62/147,793, filed Apr. 15, 2015, the contents of which are incorporated by reference in their entirety.

STATEMENT REGARDING GOVERNMENT INTEREST

This invention was made with Government support under contract K08CA160662 awarded by the National Institutes of Health. The government has certain rights in this invention.

REFERENCE TO SEQUENCE LISTING

A Sequence Listing is being submitted electronically via EFS in the form of a text file, created Apr. 14, 2016, and named "0962010120SequenceListing.txt" (13,957 bytes), the contents of which are incorporated herein by reference in their entirety.

TECHNICAL FIELD

The subject matter described herein relates to a method for treating liver-associated cancers and metastases via hepatic artery infusion of genetically modified or chimeric antigen receptor T cells (e.g., CAR-T) expressing a receptor protein which binds a tumor-specific antigen and which activates activities of the modified T-cells.

BACKGROUND

Liver metastases (LM) are cancerous tumors that have metastasized from another part of the body to the liver. Most cases of liver metastases develop from colon or rectal cancers, with approximately 60 to 70 percent of people with colorectal cancer eventually developing a liver tumor. Liver metastases are a significant cause of morbidity and mortality in patients with gastrointestinal adenocarcinoma. While hepatic resection has been considered the standard of care for patients who have resectable hepatic metastases, many patients are not candidates for resection of liver metastases. Chemotherapy is not curative for liver metastases, creating a large unmet clinical need.

Tumor infiltrating lymphocyte (TIL) studies have revealed that host T cell responses to LM are significant correlates of patient survival (Katz et al., 2013, Ann Surg Oncol, 20:946-955; Katz et al., 2010, HPB (Oxford), 12:674-683; Katz et al., Ann Surg Oncol, 16:2524-2530; Wagner et al., 2008, Ann Surg Oncol, 15:2310-2317; Turcotte et al., Canc Immunol Res, 2:530-537). While those who mount effective immune responses to LM tend to have prolonged survival, the vast majority of patients succumb to their disease in the context of endogenous immune failure. The immunosuppressive nature of the intrahepatic milieu (Cantor et al., 1967, Nature, 215:744-745; Katz et al., 2005, Hepatol, 42:293-300; Katz et al., 2004, J Immunol, 173:230-235; Katz et al., 2011, J Immunol, 187:1150-1156) may promote the development of LM and contribute to aggressive disease biology.

Accordingly, there is a need for therapeutic strategies which can facilitate host or provide immunological responses to the presence of liver metastases. Given the favorable effects of robust liver TIL responses and the inherent suppressive nature of the intrahepatic space, delivery of highly specific immunoresponsive cells for the treatment of LM is a rational approach. Described herein are compositions and methods for hepatic artery infusion (HAI) of anti-CEA CAR-Ts which can both limit extrahepatic toxicity and optimize efficacy for treatment of liver metastases.

BRIEF SUMMARY

The following aspects and embodiments thereof described and illustrated below are meant to be exemplary and illustrative, not limiting in scope.

In one aspect, a method of treating liver metastases in a subject diagnosed with having liver metastases is provided, comprising infusing into the hepatic artery of the subject a composition comprising an immunoresponsive cell which expresses a chimeric antigen T cell receptor protein (CAR), wherein the chimeric T cell receptor protein binds to an antigen expressed on metastatic cells in the liver.

In some embodiments, the immunoresponsive cell expressing the CAR is selected from the group consisting of a T cell, a hematopoietic stem cell, a natural killer cell, a natural killer T cell, a B cell and a cell of monocytic lineage. In a particular embodiment, the immunoresponsive cell is a T cell.

In some embodiments, the immunoresponsive cell is autologous to the subject. In another embodiment, the immunoresponsive cell is not autologous to the subject.

In some embodiments, the immunoresponsive cell is a T cell and the method comprises harvesting cells from the blood serum of the subject. In other embodiments, a minimum of $10^8$, $10^9$ or $10^{10}$ cells are harvested from the blood serum of the subject. In still other embodiments, the method further comprises isolating and activating peripheral blood mononuclear cells (PBMC) from the harvested cells to generate a population of autologous T cells.

In some embodiments, the method comprises transfecting the immunoresponsive cells with a nucleic acid vector which comprises a nucleic acid sequence encoding the CAR sequence to generate a population of immunoresponsive cells which expresses the CAR protein. In other embodiments, the method further comprises selecting and expanding the population of immunoresponsive cells which expresses the CAR protein. In some embodiments, the immunoresponsive cells are the population of autologous T cells.

In some embodiments, the method comprises infusing a dose of the immunoresponsive cells which express the CAR protein into the patient over a treatment period ranging from about 1 to 8 weeks, 2 to 8 weeks, 2 to 6 weeks, 2 to 4 weeks, 1 to 4 weeks, 1 to 3 weeks, 1 to 2 weeks, 3 to 6 weeks, or 4 to 6 weeks. In other embodiments, the infusing the immunoresponsive cells which express the CAR comprises infusing the cells every week, 2 weeks, 3 weeks or 4 weeks over the treatment period. In a preferred embodiment, the infusion the immunoresponsive cells which express the CAR comprises infusing CEA CAR-T cells once per week for 3 weeks.

In some embodiments, the immunoresponsive cells which express the CAR (CAR-T cells) and the CAR binds to CEA are autologous T cells. In an alternative embodiment, the immunoresponsive cells which express the CAR (CAR-T cells) and the CAR binds to CEA are nonautologous T cells.

In some embodiments, the dose of immunoresponsive cells infused into the patient is about $10^7$-$10^{10}$ or $10^8$-$10^9$ CAR-T cells. In other embodiments, the dose of immunoresponsive cells infused into the patient is about $10^7$, $10^8$, $10^9$ or $10^{10}$ immunoresponsive cells. In a preferred embodiment, the immunoresponsive cells are T cells and the CAR binds to CEA.

In some embodiments, the method comprises infusing a composition comprising the immunoresponsive cells and a pharmaceutically compatible solution, wherein the total volume of the composition ranges from about 25 ml to 125 ml, 50 ml to 75 ml, 75 ml to 100 ml, or 50 ml to 100 ml. In a preferred embodiment, the immunoresponsive cells are T cells and the CAR binds to CEA.

In some embodiments, the composition is administered to the hepatic artery by a surgical technique. In other embodiments, the composition is administered to the hepatic artery by a percutaneous technique. In still other embodiments, administering by the percutaneous technique is preceded embolization of the gastroduodenal artery and/or gastric artery.

In some embodiments, the method further comprises using angiography to confirm intrahepatic hemodynamic integrity during the infusion process.

In some embodiments, the method comprises infusing a composition comprising the immunoresponsive cells and a pharmaceutically compatible solution via a percutaneous catheter and performing liver volumetric calculations to divide the hepatic arterial dosing to reflect aberrant anatomical considerations.

In some embodiments, the method further comprises infusing a second therapeutic agent into the hepatic artery of the subject. In other embodiments, the second therapeutic agent is interleukin-2 (IL-2). In other embodiments, the second therapeutic agent inhibits suppression of the immunoresponsive cell in the subject as compared to suppression of the immunoresponsive cell in a patient not administered IL-2.

In some embodiments, the method results in a 15-50%, 20-50%, 30-50%, 40-50%, or 19 to 48% decrease in serum CEA as compared to CEA levels prior to the administration of the IL-2 to the subject. In another embodiment, the decrease in serum CEA occurs with 1, 2, 3, 4 or 5 days after the infusion.

In some embodiments, the IL-2 is administered in a continuous systemic dose ranging from about 25,000 to 150,000 IU/kg/day, 25,000 to 75,000 IU/kg/day, 50,000 to 100,000 IU/kg/day for the duration of the CAR-T treatment period. In other embodiments, the IL-2 is administered in a continuous systemic dose of about 25,000, 35,000, 40,000, 50,000, 60,000, 75,000, 85,000 or 100,000 IU/kg/day. In a preferred embodiment, the IL-2 is administered in a continuous systemic dose of about 50,000 IU/kg/day.

In some embodiments, the infusing the second therapeutic agent is performed before, during or after the infusion of the immunoresponsive cell which expresses a chimeric T cell receptor protein.

In some embodiments, the method further comprises administering to the subject radiation therapy into the hepatic artery of the subject. In other embodiments, the radiation therapy comprises administration of a plurality of microspheres containing yttrium-90 ($^{90}$Y). In still other embodiments, the administering radiation therapy comprises administering about 1 to 4 gigabecquerels (GBq), 1 to 3 GBq, 2 to 4 GBq, 3 to 4 GBq, or 2 to 3 GBq of radioactivity. In yet other embodiments, the administering radiation therapy comprises administering about 1 GBq, 1.5 GBq, 2 GBq, 2.5 GBq, 3 GBq, 3.5 GBq, or 4 GBq of radioactivity.

In some embodiments, the administering the radiation therapy comprising administering the radiation therapy about 1 week, 2 weeks, or 3 weeks after the last of the CAR-T infusions.

In some embodiments, the subject is diagnosed with a metastatic disease localized to the liver. In other embodiments, the metastatic disease is a cancer. In still other embodiments, the cancer metastasized from a primary tumor in the breast, colon, rectum, esophagus, lung, pancreas and/or stomach. In still other embodiments, the subject is diagnosed with unresectable metastatic liver tumors. In yet other embodiments, the subject is diagnosed with unresectable metastatic liver tumors from primary colorectal cancer. In some embodiments, the subject is diagnosed with hepatocellular carcinoma.

In some embodiments, the subject is diagnosed with a liver metastases, wherein the malignant cells of the liver metastases have been demonstrated to express the carcinoembryonic antigen (CEA) protein.

In some embodiments, the method results in a decrease in tumor burden in the liver of the subject. In other embodiments, the decrease in tumor burden is measured using positron emission tomography (PET), magnetic resonance imaging (MRI) or biopsy. In still other embodiments, wherein the tumor burden is measured 1-8 weeks, or about 1, 2, 3, 4, 5, 6, 7 or 8 weeks after the treatment period. In yet other embodiments, the decrease is measured relative to the tumor burden prior to infusing the dose of CAR-T cells.

In some embodiments, the tumor burden measured 1-8 weeks, or about 1, 2, 3, 4, 5, 6, 7 or 8 weeks after the treatment period is no more than 50% to 90% of the tumor burden prior to the infusion of the first dose of CAR-T cells.

In some embodiments, a method for decreasing the tumor burden in a subject diagnosed with liver metastases is provided comprising administering to the subject a CAR-T cells as described herein. In other embodiments, the tumor burden is decreased to an amount that is less than about 10%, 20%, 30%, 40%, 50%, 60%, 70%, 80% or 90% of the tumor burden prior to the administering the CAR-T cells to the subject.

In some embodiments, a method for decreasing amounts of CEA in the blood serum of a patient diagnosed with liver metastases is provided comprising administering to the subject a CAR-T cells as described herein. In other embodiments, the amount of CEA is decreased to an amount which is less than about 10%, 20%, 30%, 40%, 50%, 60%, 70%, 80% or 90% of the amount of CEA in the subject prior to administering the CAR-T cells.

In some embodiments, the chimeric T cell receptor protein comprises an extracellular domain which specifically binds to a tumor antigen expressed on the surface of the metastatic cells in the liver. In other embodiments, the chimeric T cell receptor protein comprises an extracellular domain which specifically binds to the carcinoembryonic antigen (CEA) protein.

In some embodiments, the chimeric T cell receptor protein comprises, in an N-terminal to C-terminal direction, a CEA-binding IgG immunoglobulin domain, a CD8 hinge domain, a CD28 extracellular domain, a CD28 transmembrane domain, a CD28 cytoplasmic domain and a CD3 zeta cytoplasmic domain.

In some embodiments, the CEA-binding IgG immunoglobulin domain comprises SEQ ID NO:1.

In some embodiments, the CD8 hinge region comprises a sequence which is 12 amino acids in length and which is at least 75%, 83%, 91%, or 100% identical to the sequence of residues 169-180 of SEQ ID NO:2.

In some embodiments the CD28 extracellular domain comprises a sequence which is 40 amino acids in length and which is at least 92%, 95%, 97%, or 100% identical to the sequence of residues 113-152 of SEQ ID NO:4.

In some embodiments the CD28 transmembrane domain comprises a sequence which is 27 amino acids in length and which is at least 88%, 92%, 96%, or 100% identical to the sequence of residues 153-179 of SEQ ID NO:4.

In some embodiments the CD28 signaling domain comprises a sequence which is 41 amino acids in length and which is at least 90%, 92%, 95%, 97%, or 100% identical to the sequence of residues 180-220 of SEQ ID NO:4.

In some embodiments, the zeta cytoplasmic domain comprises a sequence which is 113 amino acids in length and which is at least 90%, 95%, 97%, 98%, 99%, or 100% identical to the sequence of residues 52-164 of SEQ ID NO:3.

In some embodiments, the chimeric T cell receptor protein further comprises a signal sequence at the N-terminus of the T cell receptor protein. In other embodiments, the signal peptide is at least 84%, 89%, 94% or 100% identical to SEQ ID NO:6.

In some embodiments, the method is HITM® HEPATIC IMMUNOTHERAPY FOR METASTASES.

DETAILED DESCRIPTION

Figure 1:
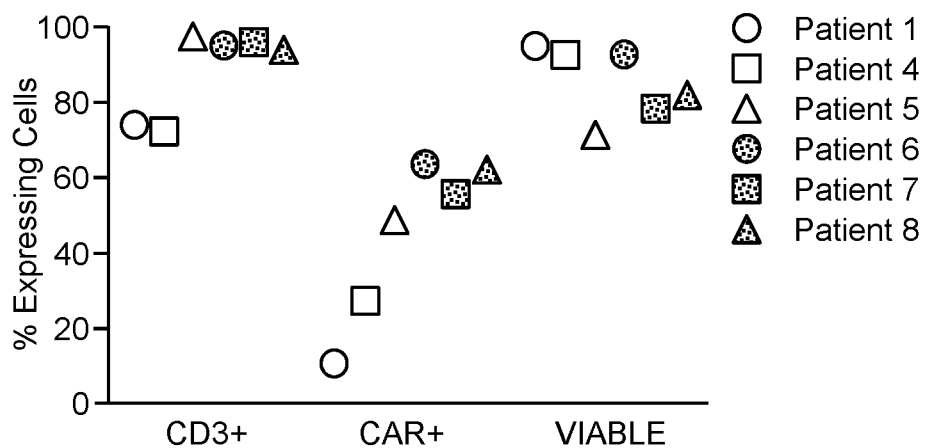
FIG. 1 illustrates mean percentages of CD3+ and CAR+ cells in patients prior to infusion of modified immunoresponsive cells.

Various aspects now will be described more fully hereinafter. Such aspects may, however, be embodied in many different forms and should not be construed as limited to the embodiments set forth herein; rather, these embodiments are provided so that this disclosure will be thorough and complete, and will fully convey its scope to those skilled in the art.

I. Definitions

As used in this specification, the singular forms "a," "an," and "the" include plural referents unless the context clearly dictates otherwise. Thus, for example, reference to a "polymer" includes a single polymer as well as two or more of the same or different polymers, reference to an "excipient" includes a single excipient as well as two or more of the same or different excipients, and the like.

Where a range of values is provided, it is intended that each intervening value between the upper and lower limit of that range and any other stated or intervening value in that stated range is encompassed within the disclosure. For example, if a range of 1 mL to 8 mL is stated, it is intended that 2 mL, 3 mL, 4 mL, 5 mL, 6 mL, and 7 mL are also explicitly disclosed, as well as the range of values greater than or equal to 1 mL and the range of values less than or equal to 8 mL.

The terms "patient," "subject," "individual," and the like are used interchangeably herein, and refer to any animal or cells thereof whether in vitro or in situ, amenable to the methods described herein. In certain non-limiting embodiments, the patient, subject or individual is a human.

The term "therapeutic" as used herein means a treatment and/or prophylaxis. A therapeutic effect is obtained by suppression, remission, or eradication of a disease state.

To "treat" a disease as the term is used herein, means to reduce the frequency or severity of at least one sign or symptom of a disease or disorder experienced by a subject.

The term "transfected" or "transformed" or "transduced" as used herein refers to a process by which exogenous nucleic acid is transferred or introduced into the host cell. A "transfected" or "transformed" or "transduced" cell is one which has been transfected, transformed or transduced with exogenous nucleic acid. The cell includes the primary subject cell and its progeny.

As used herein the term "therapeutically effective" applied to dose or amount refers to that quantity of a compound or pharmaceutical composition (e.g., a composition comprising immune cells such as T lymphocytes and/or NK cells) comprising a chimeric receptor of the disclosure, and further comprising a drug resistance polypeptide that is sufficient to result in a desired activity upon administration to a subject in need thereof. Within the context of the present disclosure, the term "therapeutically effective" refers to that quantity of a compound or pharmaceutical composition that is sufficient to delay the manifestation, arrest the progression, relieve or alleviate at least one symptom of a disorder treated by the methods of the present disclosure. Note that when a combination of active ingredients is administered the effective amount of the combination may or may not include amounts of each ingredient that would have been effective if administered individually.

As used herein, the expression "tumor load" or "tumor burden" refers to the number of cancer cells, the size of a tumor, or the amount of cancer in the body of a subject.

The term "chimeric receptor" as used herein is defined as a cell-surface receptor comprising an extracellular ligand binding domain, a transmembrane domain and one or more cytoplasmic co-stimulatory signaling domains in a combination that is not naturally found together on a single protein. This particularly includes receptors wherein the extracellular domain and the cytoplasmic domain are not naturally found together on a single receptor protein. The chimeric receptors of the present disclosure are intended primarily for use with T cells and natural killer (NK) cells. A chimeric receptor described herein may also be referred to herein as a chimeric antigen receptor (CAR), a chimeric ligand receptor, or a chimeric T cell receptor.

As used herein, the expression "specifically binds" in reference to a chimeric T cell receptor means that the chimeric T cell receptor binds to its target protein with greater affinity that it does to a structurally different protein(s).

II. Hepatic Artery Infusions of Car-T Cells

Studies have demonstrated that liver metastases (LM) patients with robust T cell responses have significantly improved outcomes, however, most LM patients fail to mount effective intrahepatic anti-tumor immunity (Katz et al., 2003, Ann Surg Onc, 20:946-955). Chimeric antigen receptor modified T cells (CAR-T), highly specific immunotherapeutic products designed to target specific tumor antigens, hold promise in providing needed anti-tumor immunity, especially in patients diagnosed with unresectable tumors. While administration of antigen-specific CAR-T cells have demonstrated encouraging results in early-phase clinical trials for leukemia, successful adaptation of CAR-T technology for CEA-expressing adenocarcinoma LM, a major cause of death in patients with gastrointestinal cancers, has yet to be achieved. Accordingly, a phase I clinical trial was designed and conducted as described herein to show that CAR-T technology is a viable option for the treatment of LM. Moreover, the clinical studies address inefficient intrahepatic delivery of CAR-T via systemic infusion which can limit the effectiveness of CAR-T treatments for LM. Described below are studies to test CAR-T hepatic artery infusions (HAI) to show that direct regional delivery of CAR-T to LM is safe and effective in treating LM. In summary, the data demonstrate that CAR-T HAIs are well tolerated and associated with evidence of tumor cell killing, showing that the hepatic artery infusion (HAI) of CAR-T to LM can indeed effectively treat LM in patients in need thereof.

Chimeric Antigen Receptor T Cells

T cells engineered with chimeric antigen receptors (CAR) to enable highly specific tumor recognition and killing have gained considerable attention following promising clinical results (Grupp et al., 2013, N Eng J Med, 368:1509-1518; Porter et al., 2011, N Eng J Med, 365:725-733; Sadelain et al., 2009, Curr Opin Immunol, 21:215-223). Reprogramming T cells with CAR genes provides an MHC-independent mechanism for docking with and lysing tumor cells. Such modified T cells have been alternatively termed "designer T cells," "T-bodies," or "CAR-T cells" (Ma et al., 2002, Cancer Chemotherapy & Biological Response Modifiers: Elsevier Science, pp. 319-345; Park et al., 2011, Trends Biotech, 29:550-557; Ma et al., 2014, Prostate, 74:286-296). Carcinoembryonic antigen (CEA) is an attractive target for CAR-T treatment of adenocarcinoma LM given high levels of CEA expression and the ability to measure CEA in serum (Blumenthal et al., 2007, BMC Cancer, 7:2; Midiri et al., 1985, Cancer, 55:2624-2629).

Upon antigen recognition, anti-CEA CAR-Ts proliferate, produce cytokines, and kill target cells (Emtage et al., Clin Canc Res, 14:8112-8122).

Generation of chimeric antigen receptor (CAR) proteins and immune cells (e.g., immunoresponsive or T cells) expressing these proteins is well known in the art and combines the targeting function and specificity of a ligand or antibody or fragment thereof with the anti-tumor activity of an immune cell. See for example, Sadelain et al., 2013, Cancer Discovery, 3:388-398. The chimeric antigen receptor protein generally comprises in an N-terminal to C-terminal direction: a target binding domain which specifically binds a protein expressed on the surface of a diseased target cell (e.g., a cancer cell or malignant cell present in the peritoneal cavity), a hinge domain, a transmembrane domain, and an immunomodulatory signaling domain.

In a preferred embodiment, the target binding domain of the CAR protein binds to the CEA protein. This CEA-binding protein was generated from a humanized monoclonal antibody (U.S. Pat. No. 6,676,924; Akamatsu et al., 1998, Clin Cancer Res, 4:2825-2832; Nolan et al., 1999, Clin Cancer Res, 5:3928-3941). In generating the anti-CEA CAR construct, the scFV construct was generated from the heavy and light chain variable domains using methods routine in the art and then the scFV fragment (disclosed herein as SEQ ID NO:1) was fused to other receptor domains to generate the CAR for use in the treatment methods presently described.

Preferred embodiments for each of the hinge domain, transmembrane domain and signaling domain(s) are provided in Table 1 below. In some embodiments, the CAR construct comprises in an N-terminal to C-terminal direction a CEA-binding domain, a CD8 hinge domain, a CD3 zeta chain transmembrane domain, and a CD3 zeta chain cytoplasmic domain. In preferred embodiments, the CAR construct comprises in an N-terminal to C-terminal direction a CEA-binding domain, a CD8 hinge domain, a CD28 extracellular domain, a CD28 transmembrane domain, a CD28 signaling domain and a CD3 zeta chain cytoplasmic domain. In some embodiments, the construct further comprises a signal peptide fused to the N-terminus of the target binding domain. It is understood that the signal peptide is not present in the CAR protein expressed on the administered immunoresponsive cells as it has been cleaved in vivo.

TABLE 1

| Parent Sequence | Sequence | CAR Domain |
|---|---|---|
| CD8 (SwissProt/GenBank Acc. No. P01732; SEQ ID NO: 2) | MALPVTALLLPLALLLHAARPSQFRVSP LDRTWNLGETVELKCQVLLSNPTSGCSW LFQPRGAAASPTFLLYLSQNKPKAAEGL DTQRFSGKRLGDTFVLTLSDFRRENEGY YFCSALSNSIMYFSHFVPVFLPAKPTTT PAPRPPTPAPTIASQPLSLRPEACRPAA GGAVHTRGLDFACDIYIWAPLAGTCGVL LLSLVITLYCNHRNRRRVCKCPRPVVKS GDKPSLSARYV | CD8 Hinge domain (bold, underlined sequence represents a preferred hinge domain) |
| CD3 Zeta chain (SwissProt/GenBank Acc. No. P20963; SEQ ID NO: 3) | MKWKALFTAAILQAQLPITEAQSFGLLD PK*LCYLLDGILFIYGVILTALFL*RVKFS RSADAPAYQQGQNQLYNELNLGRREEYD VLDKRRGRDPEMGGKPQRRKNPQEGLYN ELQKDKMAEAYSEIGMKGERRRGKGHDG LYQGLSTATKDTYDALHMQALPPR | CD3 Zeta domain (bold, underlined sequence represents a preferred zeta chain cytoplasmic domain; italics represents a preferred transmembrane domain) |
| CD28 (SwissProt/GenBank Acc. No. P10747; | MLRLLLALNLFPSIQVTGNKILVKQSPM LVAYDNAVNLSCKYSYNLFSREFRASLH KGLDSAVEVCVVYGNYSQQLQVYSKTGF | CD28 TM domain (bold, underlined represents a preferred extracellular |

TABLE 1-continued

| Parent Sequence | Sequence | CAR Domain |
|---|---|---|
| SEQ ID NO: 4) | NCDGKLGNESVTFYLQNLYVNQTDIYFCKIEVMYPPPYLDNEKSNGTIIHVKGKHLCPSPLFPGPSKP*FWVLVVVGGVLACYSL**　*LVTVAFHFWV*<u>RSKRSRLLHSDYMNMTPRRPGPTRKHYQPYAPPRDFAAYRS</u> | domain; italics represents a preferred transmembrane domain; underline only represents a preferred signaling domain) |

In some embodiments, the target binding domain of the chimeric receptor protein comprises the antigen-binding portion of an immunoglobulin wherein the immunoglobulin binds a protein on the surface of the diseased cell. The antigen binding domain can be any domain that binds to the cell surface antigen including but not limited to ligands to the receptor or immunoglobulin proteins such as monoclonal antibodies, polyclonal antibodies, synthetic antibodies, human antibodies, humanized antibodies, and fragments thereof. In preferred embodiments, the antigen-binding domain of the CAR is constructed from the variable domains of an antibody that is able to specifically bind the antigen when part of a CAR construct. In some instances, it is beneficial for the antigen binding domain to be derived from the same species in which the CAR will ultimately be used in. For example, for use in humans, it may be beneficial for the antigen binding domain of the CAR to comprise a fragment of a human or humanized antibody. Accordingly, in some embodiments, the antigen binding domain portion of a CAR comprises a tumor antigen binding fragment of a human or humanized antibody. In each of these embodiments, the antigen-binding domain of an antibody, such as the single-chain variable fragment (scFV) or an Fab fragment or is fused to a transmembrane domain and a signaling intracellular domain (endodomain) of a T cell receptor. Often, a spacer or hinge is introduced between the extracellular antigen binding domain and the transmembrane domain to provide flexibility which allows the antigen-binding domain to orient in different directions to facilitate antigen recognition and binding.

In some embodiments, the antigen binding moiety portion of the chimeric antigen T cell receptor targets the CEA antigen and comprises the CEA-binding domain of an antibody which has been shown to bind CEA expressed on a cell surface. The chimeric receptor construct can be generated according to methods and compositions known to the ordinarily skilled artisan. For example, a CEA CAR-T construct used in the Examples below comprises portions of the variable domain of a humanized MN14 antibody (described in U.S. Pat. No. 5,874,540, the contents of which are incorporated herein by reference it their entirety). A Fab or scFv construct can be generated from a CEA antibody according to the methods of Nolan et al. (1999, Clinical Canc Res, 5:3928-3941) to include the CEA-binding domains of the CEA antibody. In some embodiments, the CEA CAR-T construct comprises an amino acid sequence which is at least 90%, 95%, 96%, 97%, 98%, 99%, or 100% identical to SEQ ID NO: 1 shown below:

(SEQ ID NO: 1)
DIQLTQSPSSLSASVGDRVTITCKASQDVGTSVAWYQQKPGKAPKLLIY

WTSTRHTGVPSRFSGSGSGTDFTFTISSLQPEDIATYYCQQYSLYRSFG

QGTKVEIKRTVAAPSVFIFPPSDEQLKSGTASVVCLLNNFYPREAKVQW

-continued
KVDNALQSGNSQESVTEQDSKDSTYSLSSTLTLSKADYEKHKVYACEVT

HQGLSSPVTKSFNRGEC

In some embodiments, the CEA CAR-T construct further comprises a signal peptide at the N-terminus of SEQ ID NO:1 which is cleaved from the construct after in vivo expression of the CEA CAR-T construct. Signal sequences are well known to the ordinarily skill artisan and functions are to direct the translated protein to the cell surface. The signal sequence is cleaved after passage from the endoplasmic reticulum during translocation of the CAR protein to the cell surface. In other embodiments, the signal peptide has the sequence MGWSCIILFLVATATGVHS (SEQ ID NO:6). In still other embodiments, a linker sequence comprising 1, 2, 3, 4, 5 or 6 amino acids is present between the signal peptide and the CEA-binding domain.

The Fab or scFv domain can then be fused at its C-terminus via a peptide bond to a hinge domain such as that from the CD8 hinge domain (see SwissProt/GenBank Acc. No. P01732; SEQ ID NO:2). In a preferred embodiment, the hinge domain comprises a sequence which is 12 amino acids in length and is at least 83%, 91% or 100% identical to the sequence of residues 169-180 of SEQ ID NO:2. In other embodiments, the hinge domain comprises a sequence which is at least 95%, 96%, 97%, 98%, 99% or 100% identical to a continguous sequence of 10-20, 10-30, 10-40 or 10-50 residues present in residues 111-190 of SEQ ID NO:2.

The hinge domain can then be fused at its C-terminus to a transmembrane domain. In some embodiments, the transmembrane domain comprises a sequence which is from the CD3 zeta chain (GenBank/SwissProt Acc. No. P20963; SEQ ID NO:3). In this embodiment, the transmembrane domain comprises a sequence which is 20-30 amino acids or 20, 21, 22, 23 amino acids in length and is at least 85%, 90%, 95% or 100% identical to a contiguous sequence of 15-25 or 20-30 residues present in residues 31-51 of SEQ ID NO:3. In some embodiments, the transmembrane domain from the CD3 zeta chain comprises the sequence of amino acids at positions 31-51 of SEQ ID NO:3. In a preferred embodiment, the transmembrane domain of the CAR is from the CD28 protein (e.g., GenBank/SwissProt Acc. No. P10747; SEQ ID NO:4). The transmembrane domain can comprise a sequence which is 27 amino acids in length and is at least 88%, 92% or 100% identical to the sequence of residues 153-179 of SEQ ID NO:4. In other embodiments, the transmembrane domain comprises a sequence which is at least 95%, 96%, 97%, 98%, 99% or 100% identical to a contiguous sequence of 20-30, 20-40, or 20-50 residues present in the sequence of residues 150-190 of SEQ ID NO:4. When the CAR transmembrane domain as is a CD28 transmembrane domain as described above, the CAR can further comprise a CD28 extracellular domain, wherein the extracellular domain is positioned between the CD8 hinge domain and the CD28 transmembrane domain. The CD28 extracellular domain is 35-45, or about 38, 39, 40, 41, or 42 amino acids in length and is at least 92%, 95%, 97% or 100% identical to a contiguous sequence of 35-45 residues present in the sequence of residues 110-160 of SEQ ID NO:4.

The CD3 zeta chain cytoplasmic domain is present at the C-terminus of the CAR construct and comprises a sequence which is at least 90%, 93%, 95%, 96%, 97%, 98%, 99% or 100% identical to a contiguous sequence of 100-120 amino acids present in the sequence of residues 40-164 of SEQ ID NO:3. In a preferred embodiment, the zeta chain domain comprises a sequence which is at least 97%, 98%, 99% or 100% identical to residues 52-164 of SEQ ID NO:3.

In a preferred embodiment, the CAR further comprises a CD28 signaling domain C-terminal to the transmembrane domain and N-terminal to the CD3 zeta chain cytoplasmic domain. In some embodiments, the CD28 signaling domain comprises a sequence which is at least 92%, 95% or 100% identical to a contiguous sequence of 35-45 amino acids present in the sequence of residues 175-220 of SEQ ID NO:4. In a preferred embodiment, the CD28 signaling domain comprises a sequence which is at least 92%, 95% or 100% identical to residues 180-220 of SEQ ID NO:4.

In a preferred embodiment, the CAR polypeptide sequence comprises in an N-terminal to C-terminal direction: a CEA-binding domain comprising SEQ ID NO:1, a CD8 hinge domain as described above, a CD28 extracellular domain as described above, a CD28 transmembrane domain as described above, a CD28 signaling domain as described above, and a CD3 zeta cytoplasmic domain as described above. In one embodiment, this CAR sequence comprises in an N-terminal to C-terminal domain each of the following segments: SEQ ID NO:1 (CEA binding domain), residues 169-180 of SEQ ID NO:2 (CD8 hinge), residues 113-152 of SEQ ID NO:4 (CD28 extracellular domain), residues 153-179 of SEQ ID NO:4 (CD28 transmembrane domain), residues 180-220 of SEQ ID NO:4 (CD28 cytoplasmic domain), and residues 52-164 of SEQ ID NO:3 (CD3 zeta chain cytoplasmic domain) (alternatively referred to herein as "anti-CEA scfv-CD8α-CD28/CD3ζ"). Construction of the CAR construct using routine methods can involve the use of PCR amplification of full-length gene sequences with introduction of restriction endonuclease sites that allow digestion and ligation of the various domains to generate the desired fusion construct, but which also my encode one or more amino acids between each of the domains of the chimeric construct. Accordingly, in some embodiments, the CAR sequence comprises a linker sequence of 1, 2 or 3 amino acids between the binding and CD8 hinge domains, between the hinge and CD28 extracellular domains, between the extracellular domain and the transmembrane domains, between the transmembrane and signaling domains, between the transmembrane and zeta cytoplasmic domains, and/or between the CD28 signaling and zeta cytoplasmic domains.

Preparation of CAR-T Cells

Prior to expansion and genetic modification, a source of T cells is obtained from a subject in need of treatment for liver metastases. T cells can be obtained from a number of sources, including peripheral blood mononuclear cells, bone marrow, lymph node tissue, cord blood, thymus tissue, tissue from a site of infection, ascites, pleural effusion, spleen tissue, and tumors. In certain aspects of the present disclosure, any number of T cell lines available in the art may be used. T cells can be obtained from a unit of blood collected from a subject using any number of techniques known to the skilled artisan, such as Ficoll™ separation. In a preferred embodiment, cells from the circulating blood of an individual are obtained by apheresis. The apheresis product typically contains lymphocytes, including T cells, monocytes, granulocytes, B cells, other nucleated white blood cells, red blood cells, and platelets. The cells collected by apheresis can be washed to remove the plasma fraction and to place the cells in an appropriate buffer or media for subsequent processing steps. As those of ordinary skill in the art would readily appreciate a washing step may be accomplished by methods known to those in the art, such as by using a semi-automated flow-through centrifuge according to the manufacturer's instructions. After washing, the cells may be resuspended in a variety of biocompatible buffers, such as, for example, Ca-free, Mg-free PBS, or other saline solution with or without buffer. Alternatively, the undesirable components of the apheresis sample may be removed and the cells directly resuspended in culture media.

A specific subpopulation of T cells, such as CD3+, CD28+, CD4+, CD8+, CD45RA+, and CD45RO+ T cells, can be isolated and/or enriched by positive or negative selection techniques. For example, in some embodiments, T cells are isolated by incubation with anti-CD3/anti-CD28-conjugated beads, for a time period sufficient for positive selection of the desired T cells. The skilled artisan would recognize that multiple rounds of selection can also be used in the context of this disclosure. In certain aspects, it may be desirable to perform the selection procedure and use the unselected cells in the activation and expansion process. Unselected cells can also be subjected to further rounds of selection.

In some embodiments, a T cell population can be selected that expresses one or more of IFN-γ, TNFα, IL-17A, IL-2, IL-3, IL-4, GM-CSF, IL-10, IL-13, granzyme B, and perforin, or other appropriate molecules, e.g., other cytokines. Methods for screening for cell expression can be determined, e.g., by the methods described in PCT Publication No.: WO 2013/126712. T cells may be activated and expanded generally using methods as described, for example, in U.S. Pat. Nos. 6,352,694; 7,232,566; 6,797,514; 6,867,041; and U.S. Patent Application Publication No. 20060121005.

For the preparation of CAR-T cells for use in treating subjects diagnosed with liver metastases, patients undergo leukapheresis to harvest a minimum of $4\times10^9$ T cells, with an ideal target of about $6\times10^9$ T cells. The initial assessment of T cell numbers in the leukapheresis product can be performed at 2 hours and repeated thereafter as deemed necessary. Cells are purified to retrieve peripheral blood mononuclear cells (PBMC), alternatively referred to herein as lymphocyte-rich (PBL). The lymphocytes are activated by exposure to 50 ng/ml OKT3 and 3000 IU/mL IL-2 (Walker et al., 1993, 4:659-680). The activated cells are transduced with high titer supernatant of retrovirus containing recombinant chimeric CAR as described above with 10 μg/mL protamine (Cornetta et al., 1989, 23:187-194). On the following day, the procedure is repeated to increase the fraction of transduced cells. Two days following transduction a small aliquot of the cells is analyzed by flow cytometry for expression of the transgene. If the fraction of transduced cells is less than 10%, the cells can be allowed to undergo two more rounds of transduction and again analyzed by flow cytometry for percentage of transduced cells. When adequate numbers of T cells have been transduced (e.g., >10%) the cells are cultured, e.g., at $1.2\text{-}1.5\times10^6$/mL under activation conditions (above). The remainder of activated cells is maintained until the transduction results are known, and used for a second attempt if necessary. The transduced T cells are expanded in culture and monitored for growth/transduction parameters (doubling time, total cell numbers, % transduction, T cell activation indicators). Prior to freeze storage of the cells, 10% DMSO, 20% human serum and 3000 IU/ml of IL-2 is added. The decision on when to harvest cells is based on the presence of sufficient total cells, such that enough cells will remain in culture after harvest to be expanded for future infusions. Typically, the interval from T cell activation to dose harvesting ranges from 2-3 weeks. During expansion, flow cytometry is performed to document the presence of T cells expressing chimeric receptor. Other tests will include viability, sterility, and standard cytotoxicity assays against CEA+ and CEA- targets. Up to three attempts are made with patient T cells to achieve adequate transduction efficiencies and cell numbers to constitute a dose. In some embodiments, cells expanded from different transductions are pooled to achieve the dose.

Therapeutic CAR-T cells can be engineered to express CAR nucleic acid constructs by transfecting a population of lymphocytes with an expression vector encoding the CAR construct. Appropriate means for preparing a transduced population of lymphocytes expressing a selected CAR construct are well known to the skilled artisan, and include but are not limited to retrovirus, MFG vectors, adenovirus-based vectors, adeno-associated virus (AAV)-based vectors, retroviral vectors, retroviral-adenoviral vectors, and vectors derived from herpes simplex viruses (HSVs). Example 1 below describes the method used to generate the CAR-T cells administered to the patients.

In a preferred embodiment, the T cells are transfected with a retrovirus harboring the desired CAR construct. The MFG retrovirus and its use in transfecting eukaryotic cells are well-known to the person having ordinary skill in the art. For generation of the CAR-T cells, an expression cassette encoding the CEA CAR can be inserted between the NcoI-BamHI sites of an MFG retroviral vector backbone. The initiation codon of the inserted sequences is located precisely at the position of the viral env initiation codon. The MFG vector, referred to as MPSV/PBSQ, can be used in which the MoMLV LTRs have been replaced with the homologous sequences from the myeloproliferative virus, and the 5' primer binding site has been replaced with the homologous sequences from a variant that utilizes tRNAglu rather than tRNApro as a positive strand primer. In some embodiments, the retroviral vector does not contain a selectable marker gene. Retroviral vector supernatant from the transfected cells can be produced using the PG13 packaging cell line. The PG13 cell line was produced by stably introducing a gibbon ape leukemia virus (GALV) helper packaging system into mouse 3T3 cells. The vector producer cell (VPC) line is made by a two-step process. First, the CAR-MFG vector is transfected into the GP+E86 ecotropic packaging cell line. Transient viral supernatant from the transfected cells is collected and used to infect PG13 cells. After infection, the PG13 cells are assayed for expression of the CAR transgene by flow cytometry. The cells are then sorted for stable expression of the CAR transgene by FACS to establish a master working cell bank, and are tested for safety, sterility, identity and absence of replication competent retrovirus (RCR). The transduced cells are frozen into quantities to make up the patient dose. In some embodiments, the appropriate quantity of CAR-T cells is stored in liquid nitrogen vapor phase in one bag containing about 50-100 mL, 75-100 mL, 75-125 mL, or about 50 mL, 75 mL, 100 mL, or 135 mL of a solution which is isotonic and pharmaceutically acceptable. In some embodiments, the solution contains about 15-25%, 15%, 20% or 25% albumin. In other embodiments, the solution contains about 5-15%, 5%, 10% or 15% dimethyl sulfoxide (DMSO). In a preferred embodiment, the solution volume is about 100 mL and contains the appropriate number of cells, about 20% albumin and about 10% DMSO. In some embodiments, about 400,000-500,000 IU or about 450,000 IU IL-2 is added to the bag prior to freezing in order to maintain cell viability prior to administration. The solution is thawed prior to administration.

Hepatic Artery Infusion (HAI) of CAR-T Cells

The studies and results disclosed herein demonstrate that administration of CAR-expressing immunoresponsive cells via hepatic artery infusion can provide therapeutic efficacy in treating cancers which have metastasized to the liver. Administration of cells which have been modified as described herein to target liver metastases, specifically metastatic cells expressing CEA, is a significantly more complex process compared with infusion of, for example, a small molecule chemotherapeutic. Normal cells, such as those in the colon, express CEA. It is important to minimize or eliminate contact of normal cells by the modified CAR-T cells to minimize or prevent destruction of healthy cells. CAR-T cells are immunologic cells which can secrete various cytokines, contributing to adverse side effects. Described below are methods to address this problem, specifically, means for minimizing exposure of the modified immunoresponsive cells to healthy cells while optimizing contact of the modified cells with diseased cells.

In a preferred embodiment, the CAR expressing immunoresponsive cells are anti-CEA CAR-T cells which were generated using T cells obtained from the subject to be treated with the engineered cells. HAI of CAR-T cells to treat patients diagnosed with liver metastases will be most effective when the modified cells are efficiently directed to the liver, where the metastatic cells are present. HAI of CAR-T was also chosen in order to minimize immune mediated damage to CEA-expressing extrahepatic tissues. Patients most likely to benefit from the CAR-T therapies are those diagnosed with liver metastases such as colorectal cancer liver metastases. However, it is understood that the therapeutic methods disclosed herein can be effective in treating patients in which the liver tumor cells or liver metastases cells express one or more proteins which are recognized by an engineered and administered CAR-T cell. Such tumor antigens include but are not limited to carbohydrate antigen (CA)19-9, carbohydrate antigen (CA) 125, and thymidine kinase. In a preferred embodiment, the chimeric receptor expressed on the surface of the CAR-T cell recognizes and binds to the well-known cancer antigen carcinoembryonic antigen. The carcinoembryonic antigen (CEA) is an oncofetal cell surface glycoprotein expressed by many malignant cell types, including but not limited to colorectal, gastric, pancreatic, lung, breast and medullary thyroid carcinoma cells. Such malignant cells that metastasize to another organ such as the liver maintain their phenotypes including the expression of CEA and are thus targets for anti-CEA immunotherapies. CEA has multiple isoforms which are well known and well-characterized in structure and sequence (e.g., GenBank Accession Numbers NP_001171742, NP_001171744, NP_001020083, and SwissProt Accession Number P13688). The present methods employ the use of immunoresponsive cells which are engineered to express a chimeric receptor protein that specifically recognizes a CEA protein as known in the art. In some embodiments, the chimeric receptor protein specifically binds to a CEA protein which comprises an amino acid sequence that is at least 90%, 95%, 98% or 99% identical to SEQ ID NO:5).

Patients treated with the CAR-T cells have been diagnosed with a cancer in the liver. In some embodiments, the patients have detectable unresectable CEA-positive liver metastasis or detectable serum CEA levels. In other embodiments, the patients failed one or more lines of conventional systemic therapy or chemotherapy. Liver MRI and PET examinations are performed prior to CAR-T treatment to determine the location and extent of the cancer or metastasis.

While infusing the modified cells directly into the hepatic artery will direct most of the modified cells to the liver, many cells will be diverted due to variations in hepatic arterial anatomy observed in as many as 40-45% of people. Branching of the proper hepatic artery into right and left hepatic arteries to supply the entire liver is seen in about 80-85% of the population. In the remainder of the population, for example, the hepatic artery may branch only to a right or only to a left hepatic artery (feeding the right or left lobe of the liver, respectively) or the proper hepatic artery may be replaced by aberrant vessels diverting some blood flow to organs other than the liver. Accordingly, it is important to map the vessels leading to the right and left lobes of the liver prior to performing a HAI and, when necessary, occluding vessels which do not lead to the liver. In some embodiments, prior to infusion, patients undergo a mapping angiogram, e.g., via a common femoral artery approach.

Methods for mapping vessels in the body are well known to the ordinarily skilled artisan. Once such mapping is completed prior to treatment, a practitioner will determine which vessels will be occluded. Occlusion is achieved, for example, through the use of microcoil embolization, which allows the practitioner to block off-target arteries or vessels, thereby optimizing delivery of the modified cells to the liver. Microcoil embolization can be performed as needed prior to administering the first dose of CAR-T cells to facilitate optimal infusion of the pharmaceutical composition comprising the CAR-T cells.

The methods described involve administration of the therapeutic CAR-T cells through a catheter which is placed directly into the hepatic artery. For example, a pharmaceutical composition comprising the therapeutic CAR-T cells are hand-injected into the hepatic artery via a syringe at a rate of <1 mL/second, <2 mL/second, or at a rate of about 1 to 2 mL/second, 1 to 3 mL/second, 1 to 5 mL/second, 1 mL/second, 2 mL/second, or 3 mL/second. Alternatively, the cells are injected by use of an infusion pump as readily known in the art at the same rates as described for hand injection. The pharmaceutical composition comprising a dose of the therapeutic CAR-T cells (e.g., about $10^8$, $10^9$ or $10^{10}$ cells) has a total volume of about 25 to 100 mL, 25 to 75 mL, 40 to 60 mL, 50 to 75 mL or 50 to 100 mL, or has a total volume of about 25 mL, 40 mL, 50 mL, 60 mL, 75 mL or 100 mL. The method as disclosed herein may further comprise performing liver volumetric calculations to ensure that the dose of modified cells administered to the patient is directed to the right and left hepatic arteries, thereby providing a therapeutically effective dose throughout the liver. Liver volumetric calculations are performed according to standard methods known to the ordinarily skilled artisan and include but are not limited to scintigraphy, ultrasound, single-photon emission computed tomography, computed tomography (CT) and magnetic resonance imaging. Once the volumetric calculations for a patient are complete, the dose or number of modified cells is divided for infusion into the right and left hepatic arteries such that the number of modified cells delivered to the right and left lobes is proportional to the volume of the right and left lobes, respectively.

In some embodiments, 50% of the total volume is infused into the patient, the CAR-T solution is agitated to ensure complete cell suspension, then the final 50% of the total volume is infused into the patient. Infusion can be performed using an 18-guage needle.

Co-Administration of IL-2

The patients receive the CAR-T infusions, e.g., weekly or every 2 weeks for the duration of the CAR-T treatment period. The CAR-T treatment period can be 2, 3, 4, 5, 6 7, 8, 9, or 10 weeks or can last from 2-10, 4-9, 2-8, 2-6, 2-4, 3-6, 4-8 or 4-6 weeks. The start of the CAR-T treatment period (Day 0) is the day that blood cells are harvested from the patient to be treated (or, alternatively, from a subject who is not the patient to be treated). Patients receiving the infusions of CAR-T cells can also be administered IL-2. IL-2 facilitates viability of the CAR-T cells after infusion, however, it is preferable to use a dose of IL-2 that does not cause or enhance adverse side effects such as fever, nausea, emesis, and/or tachycardia. In some embodiments, the IL-2 is administered continuously during the full span of the CAR-T treatment period. Such continuous infusions can be carried out using a pump reservoir and administered through a central venous catheter or other method which allows the patient to be ambulatory. IL-2 infusion can be initiated less than 1, 2 or 3 hours prior to the start of the CAR-T infusion, at the time of or during the first CAR-T infusion is started, or within about 1, 2 or 3 hours after the completion of the first CAR-T infusion.

Phase I Trial for CEA CAR-T HAI

Figure 6:
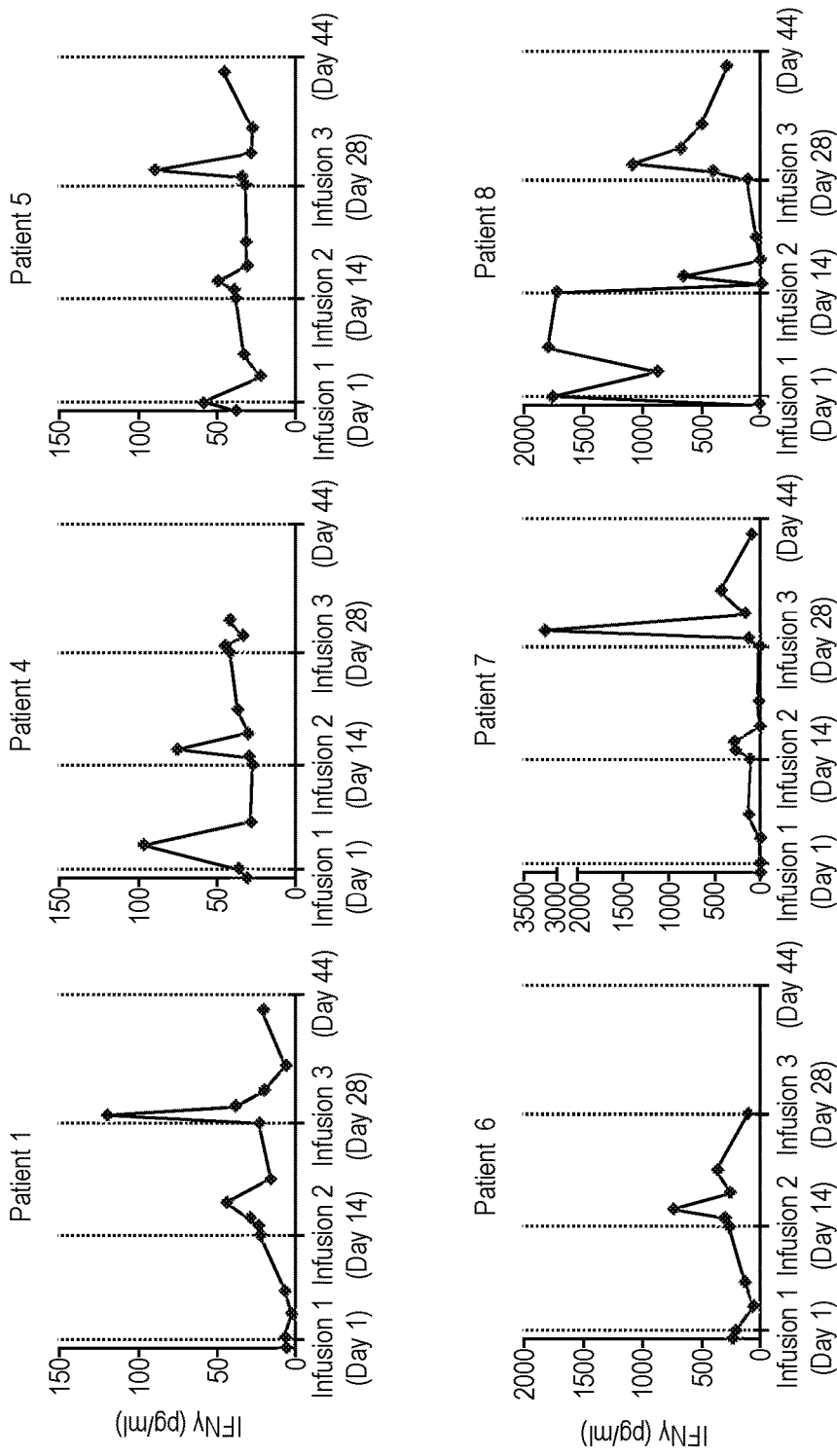
FIG. 6 illustrates IFNγ levels in patients treated according to methods described herein.

A Phase 1 clinical trial was performed in which 8 patients with liver metastases (LM) were initially enrolled and treated with anti-CEA CAR-T cells as described herein. Six of the patients completed the protocol. The patients were divided into Cohort 1 and Cohort 2. Cells were harvested from all patients on Day 0 and used to generated anti-CEA CAR-T cells (anti-CEA scfv-CD8α-CD28/CD3ζ CAR-T cells). On Day 14, 28, and 42, each of the patients in Cohort 1 received an infusion of $10^8$ cells on Day 14, $10^9$ cells on Day 28 and $10^{10}$ cells on Day 42. For Cohort 2, on Days 14, 28, and 42, each of the patients received an infusion of $10^{10}$ cells. The patients in Cohort 2 also received continuous infusion of a dose of 75,000 IU/kg/day of IL-2 beginning at Day 14 and ending on Day 55 or Day 56. On about Day 56. MRI and PET analysis of the patients in Cohorts 1 and 2 was done on Day 56. Data from the 6 patients that completed the protocol demonstrated that HAIs of anti-CEA CAR-Ts are well tolerated with and without systemic IL-2 infusion. Spikes in IFNγ were noted to occur 24 to 48 hours after doses in all patients, with or without system IL-2 (see FIG. 6). Although there were no radiographic partial or complete responses, 1 of 6 patients had stable disease and was alive for at least 24 months follow-up.

The studies described herein established the safety of anti-CEA CAR-T HAIs with and without systemic IL-2 support, reaching the maximum planned dose of $10^{10}$ cells. Accordingly, with respect to the safety and efficacy of CAR-T HAIs, the findings support use of CAR-T HAIs for treatment of LM. The limited systemic exposure of CAR-T in the study subjects likely accounted for the favorable adverse event profile. Systemic IL-2 support was associated with increased serum IFNγ levels and improved CEA responses, at the expense of more severe but manageable adverse events. As shown in Example 4, HAI led to preferential accumulation of CAR-T within liver metastases in 5 of 6 of the patients, compared with normal liver and peripheral blood. CAR-Ts were not detected in the peripheral blood in 4 of the 6 patients and only transiently in patients 7 and 8. Importantly, histologic evidence of increased LM necrosis and fibrosis were seen in the majority of subjects following CAR-T HAI (see FIG. 5). These data all show that effective delivery of the CEA CAR-T cells to the CEA+ tumor deposits correlates well with histologic evidence of tumor killing and serum cytokine surges, supporting the therapeutic efficacy of the CAR-T cells (e.g., anti-CEA scfv-CD8α-CD28/CD3ζ CAR-T cells) for the treatment of liver metastases via hepatic arterial infusion.

HAI led to preferential accumulation of CAR-T within LM in 5 of 6 HITM patients, compared to normal liver and peripheral blood. CAR-Ts were not detected in the peripheral blood in 4 of 6 patients and only transiently in patients 7 and 8. Moderate elevations of liver function test values (e.g., transient elevations of alkaline phosphatase, total bilirubin and aspartate aminotransferase levels) were likely related to the CAR-T HAI but did not result in clinically significant consequences. Systemic infusion of T cells expressing anti-CEA CAR-T was previously reported to result in dose-limiting toxicity (Parkhurst et al., 2011, Mol Ther, 19:620-626). Similar toxicities were seen in the present study with the anti-CEA CAR-T when systemically infused, particularly with IL-2 support (not shown). Continuous ambulatory infusion dose of IL-2, 75,000 IU/kg/day, is several-fold lower than what is given in other protocols (Rosenberg et al., 1999, J Clin Oncol, 17:968-975. Despite the low daily dose of the IL-2 in this study, 2 patients experienced grade 3 events requiring IL-2 dose reductions. These adverse events, including severe pyrexia and colitis, can be attributed to the IL-2 based upon the fact that the symptoms resolved promptly upon IL-2 dose reduction. In one subject, it is possible that the IL-2 activated a small number of systemically circulating anti-CEA CAR-T that mediated fever and colitis. Overall, the IL-2 infusion administration was well tolerated and the adverse events easily managed by dose reductions.

In one aspect of the present disclosure, the dose level of CEA CAR-T cells for each patient is $10^{10}$ cells administered via HAI once per week. Therapeutic efficacy of a once-per-week infusion of the cells is supported by the serum liver chemistry and cytokine data from the phase 1 trial disclosed herein. In the phase 1 study in which infusions were performed every 2 weeks, most patients demonstrated transient but clinically insignificant elevations in serum alkaline phosphatase, bilirubin, and aspartate aminotransferase (AST) levels following CEA CAR-T HAI (see Example 7). In nearly all cases, levels normalized within 3-4 days. Likewise, patients demonstrated surges in serum IFNγ and IL-6 levels following CAR-T HAI, which returned to baseline or near-baseline levels within 1 week. These data suggest that a 1-week interval is sufficient to allow for resolution of the acute inflammatory response to CAR-T HAI, and to permit safe repeat CAR-T. Changing the CAR-T interval from 2 weeks to 1 week will also minimize IL-2 exposure for the patients and allow for a more rapid return to systemic therapy for those in whom this is clinically indicated. In a preferred embodiment, patients being administered CEA CAR-T cell infusions once per week receive continuous systemic infusion of IL-2 at a dose of 50,000 IU/kg/day. In some embodiments, a patient diagnosed with unresectable liver metastases is administered a dose of 50,000 IU/kg/day IL-2 for 28 days by continuous intravenous infusion during the CAR-T infusion treatment period, inclusive of the 14 days after the final CAR-T infusion.

Therapeutic efficacy of the CAR-T treatment of liver metastases can be determined by routine imaging techniques such as magnetic resonance imaging (MRI), positron emission tomography (PET), or ultrasound. Such imaging procedures can measure the tumor burden or extent of tumor in the liver before, during and after treatment. A therapeutically effective dosing regimen for HAI of CAR-T cells can reduce tumor burden relative to the tumor burden prior to the first infusion of cells by about 10% to 100%, 10% to 80%, 10% to 60%, 10% to 40%, 20% to 40%, 20% to 60%, 20% to 80%.

CAR-T HAI with Selective Internal Radiation Therapy (SIRT)

Selective Internal Radiation Therapy (SIRT) is a form of radiation therapy generally used for patient diagnosed with unresectable cancers. SIRT is administered as radioactive microspheres into a target such as an organ, tissue or tumor in order to effectively deliver a therapeutic dose of ionizing radiation to that target resulting in damage or death of that target organ, tissue or tumor.

Radioactive microspheres for therapeutic application typically comprise a matrix material that can act as a carrier for a radionuclide material which emits ionizing radiation. In particular, it has previously been shown that a number of beta radiation emitting radionuclides, such as Phosphorus-32, Holmium-166 or Yttrium-90, can be attached to matrix microspheres such as polymeric resin or glass microspheres for injection into the blood stream of a cancer patient with therapeutic effect.

The radioactive microspheres are generally delivered via the arterial blood supply of the target tissue or tumor. To this end, a catheter is guided to the branch of the blood vessel that feeds the target tissue or tumor to infuse the microspheres into the circulation. The radioactive microspheres can be introduced into the arterial blood supply of either the whole liver, a section of the liver, or into the arterial blood supply of that part of the liver containing the tumor that is to be treated, by injection of the radioactive microspheres into the hepatic artery, the portal vein, or a branch of either of these vessels. The radioactive microspheres become trapped in the capillary beds of target tissue or tumor providing for the selective delivery of a dose of radiation to the target tissue or tumor.

Two commercially-available products available for SIRT treatment of liver cancer include TheraSphere® (MDS Nordion, Inc.), and SIR-Spheres® (SIRTeX® Medical Ltd.). Both products are Yttrium-90 labelled microspheres: Thera-Spheres® being glass microspheres having a diameter of 25±10 μm; and SIR-Spheres® being resin-based microspheres that having a diameter of 32±2.5 μm.

Despite the promising results of the phase 1 trial disclosed herein and the therapeutic efficacy of the CEA CAR-T HAI, it is always best to optimize treatment efficacy and convenience wherever possible. Combinatorial strategies can often maximize the benefit for patients diagnosed with an incurable disease. Radiotherapy induces immunogenic tumor cell death through antigen release and recruitment of effector T cells. Radiotherapy alone is only rarely capable of generating effective anti-tumor immunity. However, when combined with targeted immunotherapy agents, radiotherapy significantly contributes to a therapeutically effective anti-tumor immune response. A "HITM-SIR" trial has been designed to test the safety and potential increase in tumor killing by using SIR-Spheres® following CAR-T HAI. HITM-SIR is a novel iteration of established principles and approaches with proven safety. This novel trial has the potential to generate paradigm-changing data for the management of LM.

In one aspect, a method of treating subjects diagnosed with a liver metastasis is provided wherein the subject is treated with CAR-T HAI as described above, with or without systemic IL-2 administration, followed by administration of SIRT. Patients are dosed with SIR-Spheres equivalent to either 2 GBq, 2.5 GBq, or 3 GBq of $^{90}$Y activity based on the volume of the tumor. In some embodiments, patients with a tumor volume that is less than 25%, about 25%-50% or greater than 50% of the total liver volume are given SIR-Spheres equivalent to 2 GBq, 2.5 GBq, or 3 GBq of $^{90}$Y activity, respectively. A dose of SIR-Spheres is administered to the patient about 1 week, 2 weeks, or 3 weeks after the final CAR-T HAI infusion. In a preferred embodiment, the dose of SIR-Spheres is administered about 1 week after the final CAR-T HAI infusion.

Immunosuppressor Agents

Therapeutic efficacy of chimeric antigen receptor T cell infusions is likely to be affected by factors that lead to immunosuppression, e.g., suppression of tumor-killing cells or decreased expression of anti-tumor cytokines. It is important to consider the effects of immune environment of the intraperitoneal space in the presence of a carcinoma and to treat a patient undergoing chimeric receptor T cell therapy accordingly.

The accumulation of immunosuppressive regulatory T cells (Tregs) and myeloid derived suppressor cells (MDSCs) within the tumor microenvironment represents a potential major obstacle for the development of effective antitumor immunotherapies (Weiss et al., 2014, J Immunol., 192:5821-5829). Elimination of MDSCs has been shown to significantly improve immune responses in tumor-bearing mice and in cancer patients (Ostrong-Rosenberg et al., 2009, J Immunol, 182:4499-4506); Talmadge, 2007, Clin Cancer Rres, 13:5243-5248). Provided herein are methods for inhibiting immunosuppression by, for example, Treg and MDSC, in a patient undergoing chimeric receptor T cell therapy, wherein the patient is also administered an agent which inhibits functions of immunosuppressive cells. Both MDSC and Treg have been well described as inhibitors of endogenous T cell and CAR-T anti-tumor responses (Khaled et al., 2013, Immunol Cell Biol, 91:493-502; Burkholder et al., 2014, Biochim, Biophys Acta, 1845:182-201). IP MDSC also expressed high levels of PD-L1 (programmed death-1 receptor ligand), which was previously demonstrated to be an important mediator of CAR-T suppression (Burga et al., 2015, 64:817-829). Accordingly, in one aspect of the present disclosure, the patient receiving CAR-T HAI is also administered an immunosuppressing agent which suppresses the activity of suppressor T cells such as MDSCs or Tregs. In some embodiments, the immunosuppressing agent is an MDSC depletion antibody which binds Gr1 (granulocytic myeloid marker protein) or a PD-L1 blocking antibody.

In some embodiments, the immunosuppressing agent is an antibody that binds IL-10, PD-1 (programmed death-1 receptor), PD-L1 (programmed death-1 receptor ligand 1), PD-L2 (programmed death-1 receptor ligand 2), STAT3 (signal transducer and activator of transcription 3), GM-CSF, CD25, GITR (glucocorticoid-induced TNFR-related protein), TGF-β, or CTLA4. In other embodiments, the immunosuppressing agent is administered to the subject before infusion of the CAR-T cells. In still other embodiments, the immunosuppressing agent is administered to the subject after infusion of the CAR-T cells. The immunosuppressing agent can be administered multiple times, for example, every day, every 2 days, every 3 days, every 4 days, every 5 days, every 6 days or once per week (every 7 days) after a CAR-T HAI. The immunosuppressing agent can be administered on the same day as the infusion or can be administered 1 day, 2 days, 3 days, 4 days, 5 days, 6 days, 7 days or more prior to the first CAR-T hepatic artery infusion. More than one immunosuppressing agent can be administered to the patient, for example, the subject may be co-administered or serially administered antibodies which bind CD25 and antibodies which bind GR1.

The foregoing examples of the related art and limitations related therewith are intended to be illustrative and not exclusive. Other limitations of the related art will become apparent to those of skill in the art upon a reading of the specification and a study of the drawings.

IV. Examples

The following examples are illustrative in nature and are in no way intended to be limiting.

Example 1

Human CAR-T Cell Production

As described in more detail below, six patients (referred to herein as Patient numbers 1, 4, 5, 6, 7 and 8) were treated with hepatic infusions of CAR-T cells which specifically target metastatic cells expressing the CEA antigen on their surface. The anti-CEA scfv-CD8α-CD28/CD3ζ (Tandem) chimeric antigen receptor was cloned into the MFG retroviral backbone as previously described (FDA BB IND 10791) (Emtage et al., Clin Canc Res, 14:8112-8122, incorporated herein by reference in its entirety). Briefly, a tandem molecule was generated by molecularly fusing in an N-terminal to C-terminal direction, a hMN14 sFv (SEQ ID NO:1) of a monoclonal antibody which specifically binds CEA, a CD8 hinge segment, a CD28 extracellular domain, transmembrane domain and cytoplasmic domain and a ζ cytoplasmic domain. The resultant chimeric construct was cloned into a retroviral vector and verified by restriction digestion and sequencing. The clinical retroviral vector supernatant was produced using PG13 cells to generate gibbon ape leukemia virus pseudotyped viral particles as previously described (Beaudoin et al., 2008, J Virol Methods, 148:253-259). All clinical batches were prepared at Indiana University vector production facility (Indianapolis, Ind.) and stored at −80° C. until used.

Rhode Island Blood Center personnel performed leukapheresis at the Roger Williams Medical Center (RWMC, Providence, R.I.). Anti-CEA CAR-Ts were prepared at the RWMC Cell Immunotherapy and Gene Therapy (CITGT) Good Manufacturing Practice (GMP) Facility with standard operating procedures (SOPs) for processing, manufacturing, expansion, dose harvesting, labeling, storage and distribution. Briefly, patient peripheral blood mononuclear cells (PBMCs) were isolated from leukapheresis product using Ficoll (Sigma, St; Louis, Mo.). We then activated PBMCs for 48-72 hours in tissue culture flasks (BD Falcon, Franklin Lakes, N.J.) containing AIM V media (Life Technologies, Grand Island, N.Y.) supplemented with 5% sterile human AB serum (Valley Biomedical, Winchester, Va.), 50 ng/mL of anti-CD3 monoclonal antibody (OKT3; Ortho Biotech, Horsham, Pa.) and 3000 U/mL of IL-2 (Prometheus, San Diego, Calif.).

Using the spinoculation method (Quintas-Cardama et al., 2007, Hum Gene Ther, 18:1253-1260), 7.2-14.4×10$^8$ T cells obtained from patients were transduced in retronectin (Takara Bio Inc, Japan) coated 6-well plates in AIM V media with 5% human AB serum, 3000 U/mL of IL-2, and protamine sulfate (MP Biomedicals) at low speed centrifugation for 1 hour at room temperature. The transduction step was carried out a total of three times over 24-hrs. After transduction, cells were washed in media and incubated for 48-72 hours at 37° C. CAR-Ts were further expanded in Lifecell tissue culture bags (Baxter, Deerfield, Ill.) for 10-14 days. CAR-T growth curves and cell viability were examined periodically and cell growth media was replaced as required. CAR-Ts were examined by flow cytometry with fluorescently labeled antibodies specific for CD3 (UCHT1, Invitrogen, Frederick, Md.), CD4 (SK3, BD Biosciences, San Jose, Calif.), CD8 (3B5, Invitrogen), and CAR expression (WI2 antibody, Immunomedics, Norris Plains, N.J.). The WI2 antibody was prepared as an APC conjugate (WI2-APC; Molecular Probes). Flow cytometry was performed on a CyAn (Beckman Coulter, Brea, Calif.) or LSR-II (BD Biosciences, San Jose, Calif.) machine. In vitro activity of patient products was measured by bioluminescence cytotoxicity assay. Luciferase-expressing CEA+ tumor cells were mixed with anti-CEA CAR-T at various ratios in 96-well round bottom plates and loss of bioluminescence from each well measured (Karimi et al., 2014, PLoS One, 9:e89357). Transduced T cells were cultured and expanded in the presence of IL-2 (500 IU/mL), and CAR expression levels were checked 48 hours after transduction.

Figure 2:
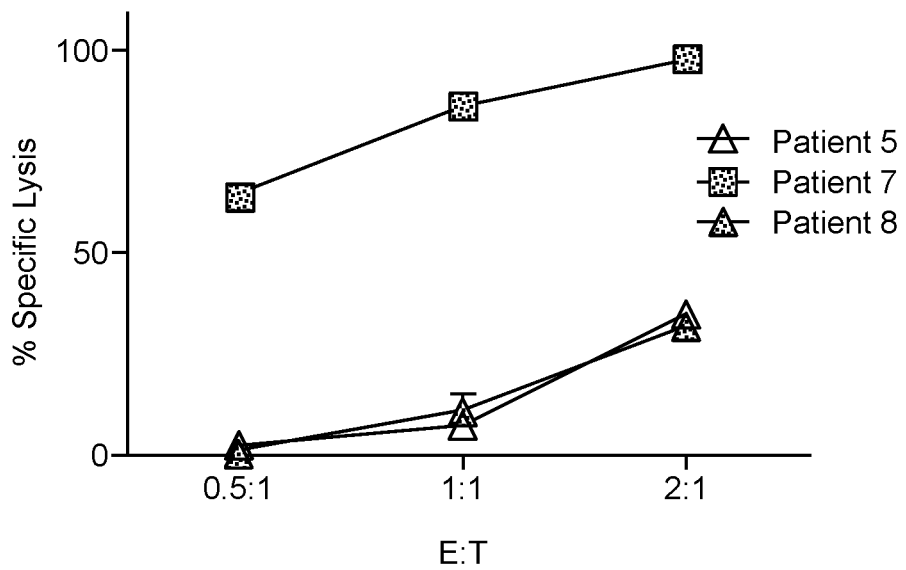
FIG. 2 illustrates results of an assay to test patient product killing of CEA+ target cells.

To assess the CAR-T cells, the leukapheresis product from each patient was analyzed by flow cytometry prior to and following transduction with anti-CEA CAR construct. For Patients 1, 4, 5, 6, 7 and 8, the mean percentage of CD3+ cells following leukapheresis was 55% (range, 12.0-82.0) and increased to 91% (range, 72-97) following activation and transduction (FIG. 1). The mean CD4:CD8 ratio was 2.4 (range, 1.4-4.7) in the leukapheresis samples and 0.8 (0.2-2.2) in the final products (not shown). The transduction efficiency (CAR+) ranged from 10% to 64%, with a mean of 45% (FIG. 1). Negligible FoxP3 staining was detected among CAR+ T cells prior to infusion (not shown). Cells in the final products were 85% viable prior to infusion (range, 71-95). In vitro cytotoxicity assays were performed to test patient product killing of CEA+ target cells. Anti-CEA CAR-T cells were cultured with CEA+MC38 colorectal carcinoma target cells. Target cell killing was quantified by loss of bioluminescence following addition of luciferin. Specific lysis was calculated based on residual photon counts. These assays confirmed that patient products specifically lysed CEA+ target cells (FIG. 2).

Clinical doses were prepared using a Fenwal cell harvester system (Baxter, Deerfield, Ill.) in freezing media containing PlasmaLyte (Baxter), 20% human bovine albumin (Valley Biomedicals), 10% DMSO (Bioniche Pharma, Lake Forrest, Ill.) and IL-2. Bacterial and fungal cultures were monitored for 14 and 28 days respectively. Assays for bacterial endotoxin were performed using LAL Endotoxin assay kits (Lonza, Walkersville, Md.). The clinical dose was stored in liquid nitrogen and thawed immediately prior to infusion.

Example 2

Clinical Study Design

A phase I clinical study (NCT01373047, RWH 11-335-99) was performed. The study enrolled eight patients with unresectable CEA+ adenocarcinoma LM who progressed on an average of 2.5 (range 2-4) lines of conventional systemic therapy (Table 2).

TABLE 2

Patient Characteristics

| ID | Sex | Age | Dx | Chemo | DFI | EHD | #LM | Size (cm) | CEA (ng/ml) | IL-2 | CAR-T Doses |
|---|---|---|---|---|---|---|---|---|---|---|---|
| 1 | F | 56 | Colon | 4 | 0 | None | >10 | 14.4 | 3265 | No | 3 |
| 2 | M | 52 | Colon | 2 | 0 | Lungs | >15 | 12.6 | 352 | No | 0^ |
| 3 | M | 52 | Gastric | 1 | 0 | None | 1 | 5.7 | 29.9 | No | 0^^ |
| 4 | M | 55 | Ampullary* | 2 | 9 | Lungs, RPN | 1 | 1.7 | 362 | No | 3 |
| 5 | M | 63 | Colon | 3 | 37 | None | 2 | 5.7 | 2** | No | 3 |
| 6 | M | 51 | Colon | 3 | 36 | Lungs | >10 | 10.5 | 1112 | Yes | 3 |
| 7 | F | 53 | Colon | 3 | 0 | Lungs | >10 | 8.0 | 32 | Yes | 3 |
| 8 | M | 66 | Colon | 2 | 0 | Lungs | >10 | 9.8 | 72 | Yes | 3 |
| | | Mean = 57 | | Mean = 2.5 | | | | Mean = 8.4 | Mean = 807.2 | | |

DFI = disease free interval from diagnosis of primary to liver metastases; LM = liver metastases; SIZE = largest LM prior to CAR-T treatment; IL-2 = continuous IL-2 infusion with CAR-T; RPN = retroperitoneal nodes;
*= pancreatobiliary subtype of ampullary carcinoma;
^= withdrew after 2 doses due to extrahepatic progression;
^^= withdrew due to unrelated medical condition;
**= CEA expression confirmed in tumor specimen by immunohistochemistry.

Six patients completed the protocol (FIG. 3), one patient withdrew due to an unrelated infection prior to treatment, and another patient withdrew due to extrahepatic disease progression prior to his third CAR-T HAI. Of the patients that completed the protocol, 4 were male and 2 were female. Five patients had stage IV colorectal carcinoma and one patient had pancreatobiliary ampullary carcinoma. The average age was 57 (range, 51-66). Patients presented with substantial disease burdens, with the average size of the largest LM being 8.4 cm (range, 1.7-14.4) and five patients having more than 10 LM. The mean CEA level upon enrollment was 807 ng/ml (range, 2-3265). Five of eight patients had synchronous colorectal LM and the mean disease-free interval was 27.3 months (range, 9 to 37) for patients with metachronous LM. All further analyses include only the six patients who completed the study.

Figure 3:
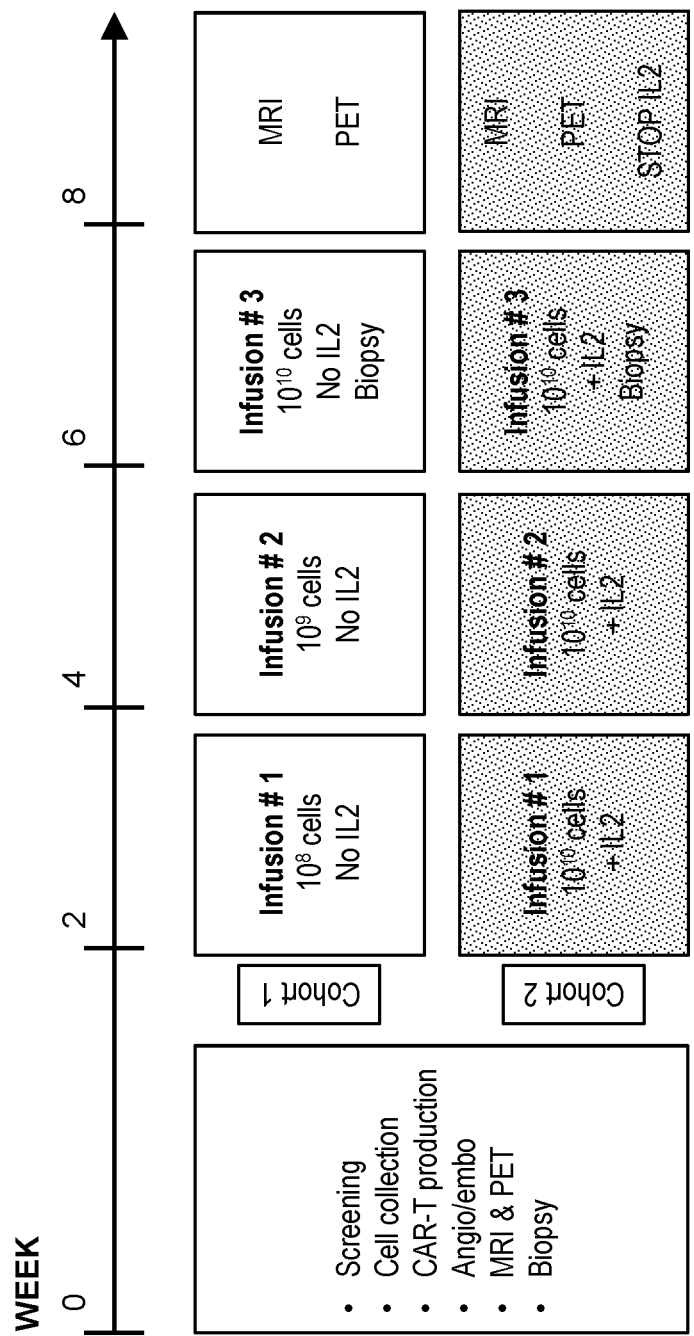
FIG. 3 illustrates a phase 1 clinical trial protocol to test therapeutic efficacy of modified immunoresponsive cells as described herein.

In the study, two cohorts of three patients were treated with anti-CEA CAR-T HAIs without or with systemic IL-2 support (FIG. 3). Cohort 1 (Patients 1, 4 and 5) was treated with CAR-T HAIs in intrapatient dose escalation fashion ($10^8$, $10^9$, and $10^{10}$ cells) without IL-2. Specifically, T cells were collected from each patient on Day 0, the first infusion was on Day 14 during which $10^8$ cells were infused, the second infusion was on Day 28 during which $10^9$ cells were infused and the third infusion was on Day 44 during which $10^{10}$ cells were infused. Those in the cohort 2 (Patients 6, 7 and 8) received 3 HAI of $10^{10}$ CAR-Ts on Days 14, 28 and 44 in addition to continuous systemic IL-2 infusion at 75,000 U/kg/day via an ambulatory infusion pump for 6 weeks beginning at the time of the first infusion on Day 14.

Eligible patients had measurable unresectable CEA-positive LM or detectable serum CEA levels and failed one or more lines of conventional systemic therapy. Minimal extrahepatic disease in the lungs or abdomen was permitted. Clinical assessments were performed at baseline, on infusion days, and 1, 2, 4, and 7 days post-infusion. Planned imaging assessments with liver MRI and PET examinations were scheduled within one month prior to the first infusion and then within one month following the third CAR-T HAI. The study radiologist (BS) graded responses according to modified RECIST (mRECIST) and immune related response criteria (Wolchok et al., 2009, Clin Cancer Res, 15:7412-7420). A blinded pathologist scored tumor necrosis and fibrosis on slides from percutaneous biopsies performed prior to treatment and two weeks following the second dose. Safety evaluation was performed per protocol. Severity of adverse events was graded using the National Cancer Institute Common Terminology Criteria for Adverse Events version 3.0.

Example 3

CAR-T Cell Hepatic Arterial Infusion

At baseline, a mapping angiogram was performed via a right common femoral artery approach. The gastroduodenal and right gastric arteries, in addition to other potential sources of extrahepatic perfusion, were embolized with microcoils. For CAR-T infusions, the same arterial access procedure was carried out and the cells were hand-injected via a 60 cc syringe at a rate of <2 cc/second with a total volume of 100 cc. Angiography with calibrated contrast rate was performed after the first 50 cc and at completion of the CAR-T infusion to confirm preserved arterial flow. Infusions were delivered into the proper hepatic artery when possible. In cases of aberrant hepatic arterial anatomy, where either the right or left hepatic artery did not arise from the proper hepatic artery, the dose was split based upon lobar volume calculations. In such cases, split doses were delivered separately into the right and left hepatic arteries to ensure proportionate CAR-T delivery to both lobes.

The anti-CEA scfv-CD8α-CD28/CD3π (Tandem) chimeric antigen receptor used in the Examples below was cloned into the MFG retroviral backbone as previously described (FDA BB IND 10791) (Nolan, et al., 1999, Clin Cancer Res, 5:3928-394; Emtage et al., 2008, Clin Cancer Res, 14:8112-8122; see Example 1 above). Briefly, the tandem molecule was generated by molecularly fusing a fragment encoding the hMN14 sFv-CD8 hinge segment in the MFG retroviral backbone with a hybrid CD28/CD3ζ molecule. The construct was verified by restriction digestion and sequencing. The clinical retroviral vector supernatant was produced using PG13 cells to generate gibbon ape leukemia virus pseudotyped viral particles as previously described (Beaudoin et al., 2008, J Virol Methods, 148:253-259). All clinical batches were prepared at Indiana University vector production facility (Indianapolis, Ind.) and are stored at −80° C. until use.

Example 4

CAR-T Cell Trafficking Following Infusion

CT guided percutaneous biopsies were obtained in order to sample LM and normal liver prior to the first CAR-T HAI and at the time of the final HAI. The proportions of CAR-T (CAR+/total lymphocyte %) in LM biopsy, normal liver biopsy, and peripheral blood samples were determined by flow cytometry. For example, samples from patient 7 demonstrated that 1.8% of normal liver lymphocytes were CAR+ following HAI of CAR-T and 7.6% of intratumoral lymphocytes were CAR+. It was confirmed that that CAR+ cells in the post-infusion LM biopsy specimen were CD3+. CAR-T population data in peripheral blood, normal liver, and LM were determined for all patients. CAR-Ts were more abundant in the LM compared to normal liver in 5 of 6 patients. In patient 5, CAR-Ts were found to comprise 1.4% of LM lymphocytes in a sample obtained during a microwave ablation procedure 12 weeks following his final CAR-T infusion. In 4 patients, CAR-Ts were not detectable in peripheral blood but were transiently present in patient 7 and patient 8 at the time of the final infusion, and the levels dropped below detection 3 days later. Quantitative PCR was performed on peripheral blood samples taken at day 2 following the final infusion; only patient 7 had a measurable increase (1.1-fold) in CAR DNA relative to baseline. Anti-CAR antibodies were not detected in patient sera following CAR-T infusion.

Example 5

Therapeutic Activity

At last follow-up, 5 of the 6 heavily pre-treated patients who completed the trial died due to disease progression (Table 3).

TABLE 3

Patient Outcomes

| ID | IL-2 | CAR+ % | MRI | PET | ΔCEA %^ | OS (weeks) | Status |
|---|---|---|---|---|---|---|---|
| 1 | NO | 10.4 | PD | PD | −1 | 30 | DOD |
| 4 | NO | 27.2 | | | +401 | 8 | DOD |
| 5 | NO | 48.9 | SD | SD | +63 | 140 | AWD - Residual disease treated with microwave ablation and further systemic therapy |
| 6 | YES | 63.5 | PD | PD | −19 | 13.0 | DOD |
| 7 | YES | 57.4 | PD | PD | −48 | 17 | DOD - Underwent resection of obstructing primary right colon tumor after final CAR-T infusion |
| 8 | YES | 61.9 | PD | PD | −43 | 19 | DOD |

^Fold change from baseline at time of 2$^{nd}$ biopsy or IL-2 infusion disruption; SAE: serious adverse events; DOD: dead of disease; AWD: alive with disease; PD: progressive disease; SD: stable
Patient 2 withdrawn after 2 CAR-T doses due to extrahepatic progression and was DOD 23 days after 2$^{nd}$ CAR-T infusion. Patient 3 withdrawn after cell collection due to unrelated medical condition.

MRI and PET scans were performed in 5 of 6 patients at baseline and 2-4 weeks following the third CAR-T HAI. Patient 8 did not obtain final imaging following a return to his native country and ultimately died of disease progression. All patients except Patient 5 were determined to have radiographic disease progression by mRECIST and criteria. Patient 5 was found to have stable disease by MRI and PET. Patient 7 developed new lesions and demonstrated an increase in size of some pre-existing lesions, while other lesions decreased in size. The lesion in the posterior sector of Patient 7 that decreased in size on MRI was not visible on PET. More medial disease that was decreased in size on MRI was noted to become hypometabolic on the post-infusion PET for Patient 7.

Figure 4:
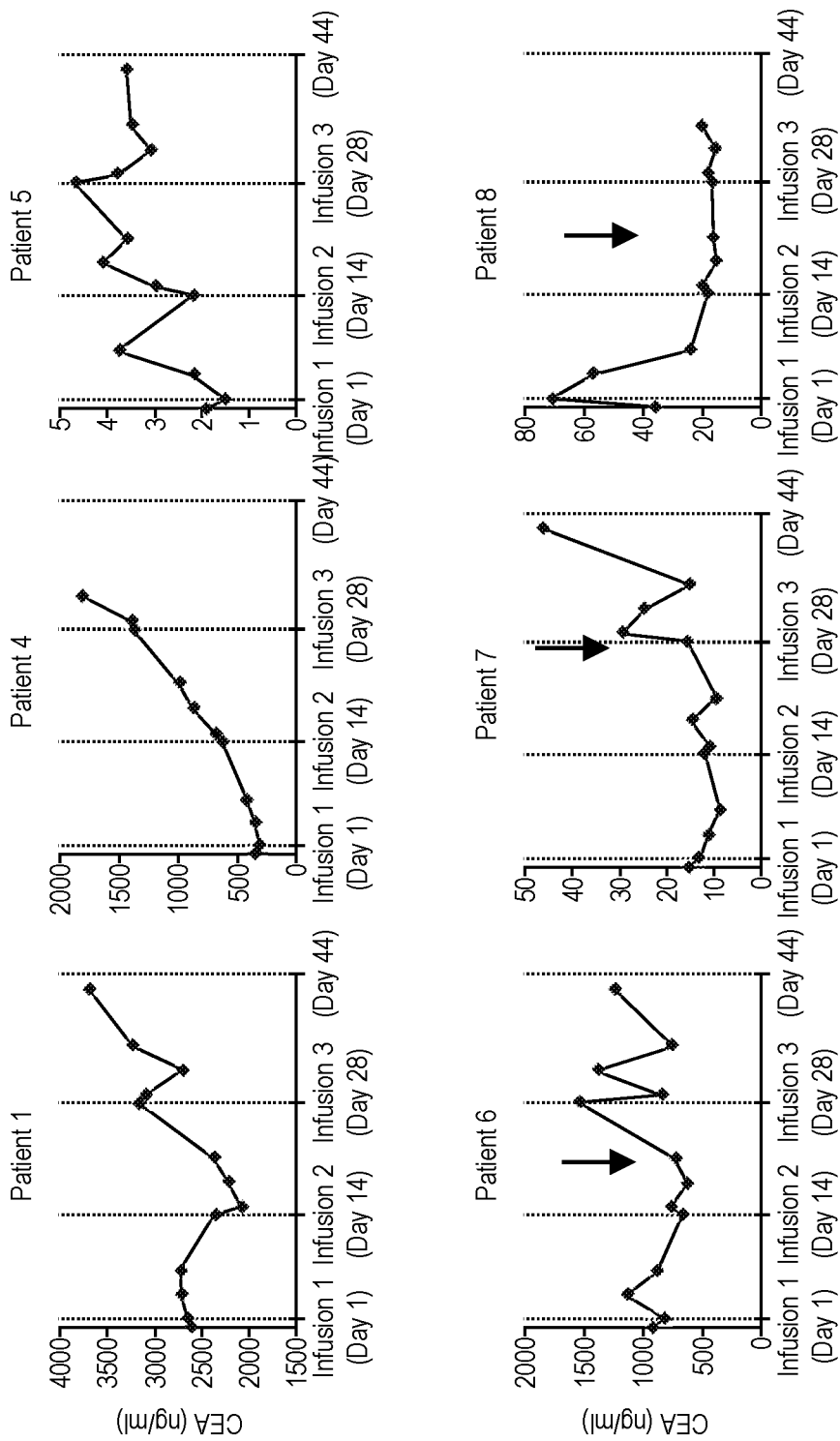
FIG. 4 illustrates serum CEA levels in patients treated according to methods described herein.

Given the limited utility for short follow-up conventional imaging following infusion of CAR-T, we measured serum CEA levels at multiple time points following each of the three HAIs for each patient. Among the patients in cohort 1, transient decreases in serum CEA were demonstrated in two patients following each CAR-T HAI (FIG. 4, Patients 1 and 5). CEA kinetics were closely paralleled by changes in serum CA19-9 levels (not shown). Patient 4, who presented with hepatobiliary subtype ampullary carcinoma, was the only patient without a CEA decrease at any point during the trial and he also had the shortest survival time.

The patients in cohort 2 who received systemic IL-2 along with anti-CEA CAR-T had more favorable CEA responses to treatment. As each of the three patients in cohort 2 required an IL-2 interruption or dose reduction, which would likely impact CAR-T function, we compared CEA levels at baseline with the time point just prior to IL-2 dose change (indicated by the arrows in FIG. 4). When using these time points, all three patients in cohort 2 had decreases in serum CEA concentrations (FIG. 4 and Table 3). Patients 7 and 8 had a 48% and 43% decrease in serum CEA concentrations, respectively, prior to IL-2 dose interruption or reduction. The mean overall survival time for the 6 patients who completed the trial was 30 weeks with a median of 15 weeks (range, 8-73). Patient 5 is alive with disease at 24 months following his final CAR-T HAI. Following completion of the HITM trial, Patient 5 was determined to have stable disease and we performed a microwave ablation of residual unresectable tumor.

Figure 5:
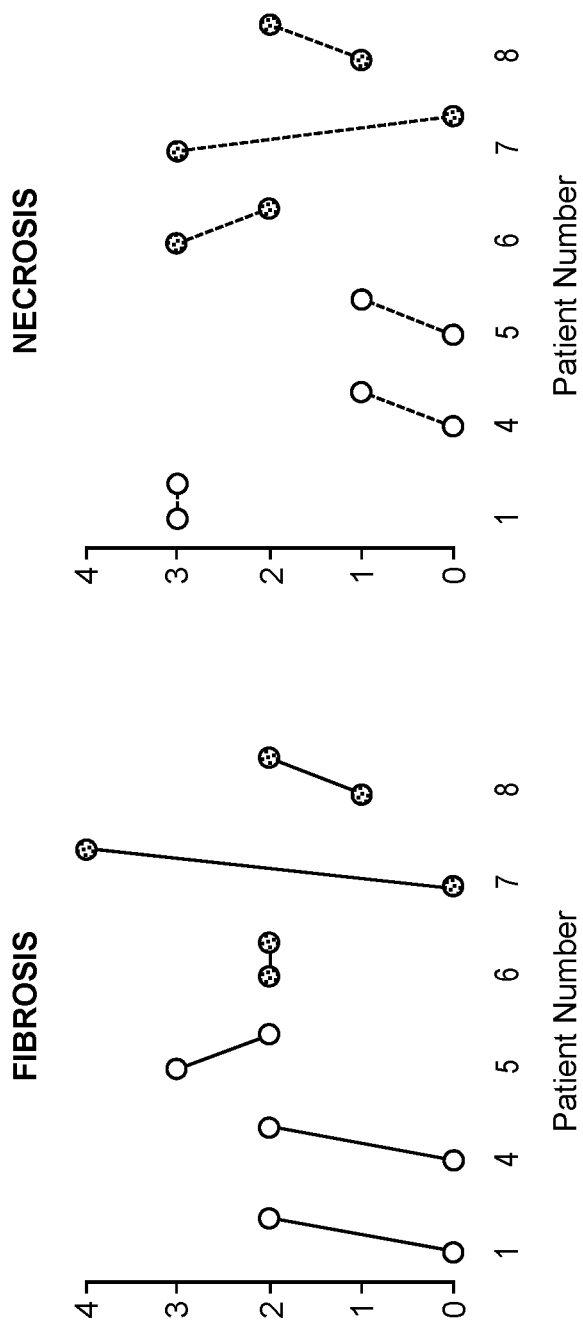
FIGS. 5A-5B illustrate LM fibrosis (FIG. 5A) and LM necrosis (FIG. 5B) in patients treated according to methods described herein.

Detecting radiographic responses in heavily pre-treated patients with advanced metastatic disease is challenging, and even more so with immunotherapy where intratumoral inflammation and edema may minimize the relevance of standard RECIST criteria (Wolchok et al., 2009, Clin Canc Res, 15:7412-7420). As such, we obtained LM biopsies prior to and following CAR-T HAIs to assess degrees of intratumoral necrosis and fibrosis. Normal liver and liver metastasis core needle (16-gauge) biopsies were obtained under sonographic guidance at baseline and at the time of the third CAR-T HAI. Three cores were obtained for normal liver and liver metastases, with each confirmed by cytology. For each case, 4- to 5-mm sections were stained with hematoxylin and eosin (H&E) and additional unstained slides were stained with anti-CEA antibody (TF 3H8-1; Ventana). All immunohistochemical stains were performed on the Ventana Medical System at Our Lady of Fatima Hospital (Providence, R.I.). All slides were reviewed in blinded fashion and graded for necrosis and fibrosis. Fibrosis was scored as follows: 0%, grade 0; 5% to 10%, grade 1; 11% to 50%, grade 2; >50%, grade 3. Necrosis was scored as follows: 0%, grade 0; 0% to 10%, grade 1; 11% to 50%, grade 2; >50%, grade 3. Flow cytometry was performed on fresh biopsy tissue for CAR-T cells and peripheral blood as described above. After review by a blinded pathologist, 4 patients had an increase in intratumoral fibrosis and 3 patients were scored as having an increase in necrosis within their LM (FIG. 5). For each patient, baseline and post infusion scores are shown from left to right in FIG. 5. Patients 1, 4, 7 and 8 showed an increase in fibrosis while patients 4 and 5 showed an increase in necrosis.

Example 6

Serum IFNγ Concentration and CEA Response Correlation with IL-2 Administration

Figure 7:
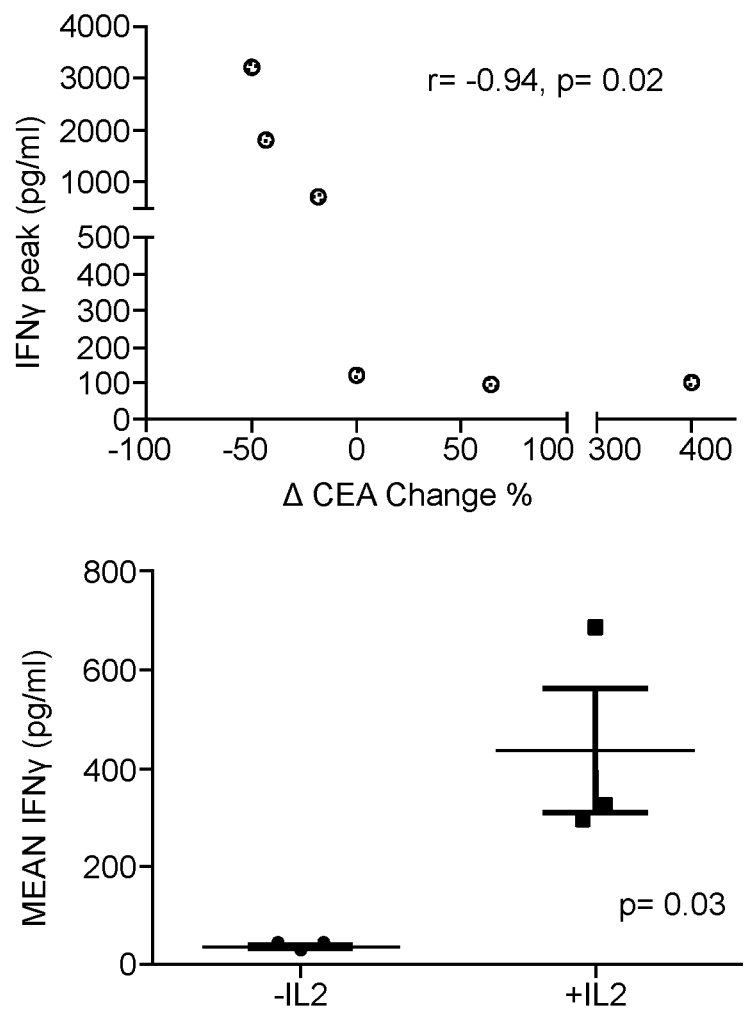
FIG. 7 illustrates peak and mean IFNγ levels in patients treated according to methods described herein.

Serum IFNγ levels were measured by ELISA at multiple time points. Spikes in IFNγ were noted to occur 24-48 hours after doses in all patients, without or with systemic IL-2 (FIG. 6; dotted vertical lines indicate CAR-T infusion time points and the first data point represents the baseline value prior to CAR-T infusion). Serum CEA changes were compared to peak change in IFNγ for each patient (FIG. 7, top). The inverse correlation between peak IFNγ levels and CEA change was significant (R=−0.94, p=0.02). All patient HAI CAR-T doses contained a quantity of IL-2 (600,000 IU). The three patients (Patient numbers 6, 7, and 8) with continuous systemic IL-2 exposure and largest CAR-T doses had the best CEA responses and the highest mean IFNγ levels (P=0.03, FIG. 7, bottom).

Example 7

Safety Data

Adverse events (AE) of any grade attributable to any cause were observed in all patients who completed the trial (Table 4). The dose in cohort 1 reached the planned maximal HAI CAR-T infusion level at $10^{10}$ cells. No CAR-T dose reductions were required in cohort 1 and therefore, all patients in cohort 2 received 3 doses at the $10^{10}$ level with IL-2 support. There were no grade 4 or 5 adverse events. Febrile AEs were observed in 4 patients. Patient 7 experienced grade 3 fever and tachycardia, with a temperature peak of 104° F. The fever and tachycardia resolved in Patient 7 after a 50% dose reduction in her systemic IL-2 infusion. Of note, Patient 7 also experienced an increase in her peripheral eosinophil count with a peak of 20% and absolute count of 3,740/ml. Given the reported association between IL-2 infusion and cardiac thrombosis with other features of Loeffler's syndrome (Junghans et al., 2001, New Eng J Med, 344:859-860), we obtained an echocardiogram and electrocardiogram which were normal. Her eosinophil count returned to normal limits without specific intervention.

TABLE 4

Adverse Events

| ID | IL-2 | Grade | # | Description |
|---|---|---|---|---|
| 1 | NO | 1 | 12 | Fever, mylagias, abdominal pain, nausea, emesis, and tachycardia |
|   |    | 2 | 2  | Abdominal wall muscle spasm and ↑ALT |
|   |    | 3 | 2  | ↑AST and ↑alk phos |
| 4* |   | 1 | 5  | Ascites, edema, thrombocytopenia, ↑ALT, ↑AST |
|    |   | 2 | 5  | ↑alk phos, leukopenia, dyspnea |
|    |   | 3 | 2  | Pleural effusion, anorexia |
| 5  |   | 1 | 2  | Fever, rash |
|    |   | 3 | 1  | Emesis |

TABLE 4-continued

Adverse Events

| ID | IL-2 | Grade | # | Description |
|----|------|-------|---|-------------|
| 6 | YES | 1 | 5 | ↑AST, ↑ALT, thrombocytopenia, dyspnea, rash |
|   |     | 2 | 1 | Lower extremity edema |
|   |     | 3 | 3 | Emesis, subscapular liver hematoma, ↑alk phos |
| 7 |     | 1 | 7 | Eosinophilia, chills, fever, abdominal pain, ↑bilirubin |
|   |     | 2 | 2 | Emesis, diarrhea |
|   |     | 3 | 3 | Tachycardia with fever (104° F.)^, emesis, abdominal pain |
| 8 |     | 2 | 6 | Fever, tachycardia, diarrhea, dehydration, lower extremity edema |
|   |     | 3 | 3 | Anemia, abdominal pain, colitis* |

*Death due to disease progression 28 days after third infusion.
^Led to IL-2 dose reduction.

Patient #2 experienced grade 3 abdominal pain and dehydration; he was taken off protocol after the 2nd HAI and died due to disease progression 23 days later. Patient #3 was withdrawn prior to CAR-T infusion due to an unrelated medical condition.

Liver function test adverse events reflect values outside of normal range and not necessarily change from baseline.

Normal liver parenchyma and biliary structures were well preserved following CAR-T HAIs. Biopsies from normal liver did not demonstrate increased levels of inflammation or fibrosis following CAR-T HAI whether or not systemic IL-2 was administered. While all patients experienced transient elevations of alkaline phosphatase (alk phos), total bilirubin, and aspartate aminotransferase levels (AST), only Patient 1 experienced grade 3 elevations and the majority of values did not deviate significantly from baseline levels. Portal pressures and liver synthetic function were not adversely affected by the CAR-T HAIs, as reflected by no patient becoming thrombocytopenic or coagulopathic.

Example 8

Safety Data

A phase I clinical study is conducted wherein patients are each administered $10^{10}$ anti-CEA scfv-CD8α-CD28/CD3ζ CAR-T cells via HAI. was performed (as described in the Examples above). T cells will be isolated from each patient on Day 0, transfected and selected to express the anti-CEA scfv-CD8α-CD28/CD3ζ construct. Each patient is then administered $10^{10}$ cells on Days 14, 21 and 28. On Day 44 (after a 2-week break following the final cell infusion), a dose of SIR-Spheres® containing is infused into each patient.

For dosing SIR-Spheres®, patients will receive a predetermined quantity of SIR-Spheres® that will vary depending on the size of the tumor volume relative to normal liver volume. Patients with tumor that was either <25%, 25%-50% or >50% of the total liver volume are given SIR-Spheres® equivalent to either 2 gigabecquerels (GBq), 2.5 GBq, or 3 GBq of $^{90}$Y activity. Provisions are made for patients in whom the lung-liver breaththrough scan indicatied that more than 10% of the microspheres passed through the liver and lodged in the lungs. The amount of $^{90}$Y activity to be administered is reduced by 2% for each 1% that the lung-liver breakthrough percentage is greater than 10%. Patients are discharged either the same day or the following day after the SIR-Spheres® treatment.

Patients are evaluated as having a complete response, a partial response, stable disease or progressive disease at one month after the final infusion by appropriate clinical and radiologic studies. Circulating levels of modified T cells are monitored by flow cytometry to detect anti-CEA scfv-CD8α-CD28/CD3 and CD4/CD3ζ and by PCR. LM and normal liver biopsy specimens are used to determine the degree of CAR-T tumor infiltration. Biopsy samples are analyzed by flow cytometry and/or immunohistochemistry to quantify the presence of anti-CEA scfv-CD8α-CD28/CD3ζ CAR-T. Samples are drawn for serum cytokine levels and changes in normal liver T cell populations. ELISA assays are performed to measure serum IL-2, IFNγ, IL6, IL17, and IL10. Neutrophil:lymphocyte ratios are determined at the same time points from CBCs, as well as a detailed assessment of hepatic and peripheral T cell populations by flow cytometry. Intrahepatic and peripheral T cells are stained with antibodies specific for CD3, CD4, CD8, FOXP3, PD-1, CD25, CTLA4, and CD69.

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

What is claimed is:

1. A method for treating a liver metastasis in a human subject, comprising: percutaneously infusing into the hepatic artery of the human subject a therapeutically effective amount of a composition comprising a chimeric antigen receptor T cell (CAR-T cell) which expresses a chimeric antigen receptor protein, wherein the chimeric antigen receptor protein binds to an antigen expressed on metastatic cells in the liver, wherein the chimeric antigen receptor protein comprises SEQ ID NO: 1.

2. The method according to claim 1, further comprising performing angiography to map the hepatic artery and nearby vessels prior to the infusing step.

3. The method according to claim 2, further comprising occluding vessels which do not feed into the liver.

4. The method according to claim 1, further comprising performing angiography during the infusing step, wherein the angiography monitors intrahepatic hemodynamic integrity during the infusing step.

5. The method according to claim 1, further comprising administering a second therapeutic agent into the hepatic artery of the human subject.

6. The method according to claim 5, wherein the second therapeutic agent is IL-2.

7. The method according to claim 6, wherein the administering the second therapeutic agent is performed before, during or after the infusion of the composition comprising the immunoresponsive cell.

8. The method according to claim 1, wherein the composition comprising the CAR-T cells is infused into the hepatic artery of the human subject once every 1 week, once every 2 weeks, once every 3 weeks, or once every 4 weeks.

9. The method according to claim 1, wherein the infusion into the hepatic artery of the human subject the composition comprising the CAR-T cells comprises infusing $10^8$ to $10^{10}$ CAR-T cells into the hepatic artery.

10. The method according to claim 1, wherein the infusion of the composition results in a 40% to 50% decrease in serum CEA as compared to the level of CEA in the serum prior to the infusion.

11. A method for treating a liver metastasis in a human subject, comprising: percutaneously infusing into the hepatic artery of the human subject a composition comprising a CAR-T cell which expresses a chimeric antigen receptor protein (CAR), wherein the CAR protein binds to CEA, wherein the chimeric antigen receptor protein comprises SEQ ID NO: 1.

12. The method according to claim 11, wherein the CAR comprises in an N-terminal to C-terminal direction: an scFv which binds CEA, a CD8 hinge domain, a CD28 extracellular domain, a CD28 transmembrane domain, a CD28 cytoplasmic domain, and a CD3 zeta cytoplasmic domain.

13. The method according to claim 12, wherein the infusing comprises infusing $10^8$ to $10^{10}$ CAR-T cells into the hepatic artery.

14. The method according to claim 12, further comprising administering a composition comprising a second therapeutic agent to the human subject.

15. The method according to claim 14, wherein the second therapeutic agent is IL-2 or yttrium-90.

* * * * *